(12) United States Patent
Shang

(10) Patent No.: US 9,951,081 B1
(45) Date of Patent: Apr. 24, 2018

(54) CHLORIN E6 DERIVATIVE AND PHARMACEUTICALLY ACCEPTABLE SALT THEREOF AND PROCESS FOR PREPARING AND USE OF THE SAME

(71) Applicant: Hui Liu, Changsha, Hunan (CN)

(72) Inventor: Hua Shang, Nanjing (CN)

(73) Assignee: Hui Liu, Changsha (CN)

( * ) Notice: Subject to any disclaimer, the term of this patent is extended or adjusted under 35 U.S.C. 154(b) by 0 days.

(21) Appl. No.: 15/605,620

(22) Filed: May 25, 2017

Related U.S. Application Data

(63) Continuation of application No. PCT/CN2016/112586, filed on Dec. 28, 2016.

(30) Foreign Application Priority Data

Oct. 26, 2016  (CN) .......................... 2016 1 0946874

(51) Int. Cl.
  *C07D 487/22*  (2006.01)
(52) U.S. Cl.
  CPC .................................. *C07D 487/22* (2013.01)
(58) Field of Classification Search
  None
  See application file for complete search history.

(56) References Cited

FOREIGN PATENT DOCUMENTS

| CN | 1102412 A | 5/1995 |
|---|---|---|
| CN | 104086554 A | 10/2014 |
| CN | 105384743 A | 3/2016 |

OTHER PUBLICATIONS

"Amino acid structures", http://www.neb.com/tools-and-resources/usage-guidelines/amino-acid-structures, accessed Aug. 2, 2017.*
ChemFiles Unnatural Amino Acids II, vol. 2, No. 4, 2002, no page numbers.*
Photodynamic Therapy "Photodynamic Therapy", https://www.cancer.org/treatment/treatmentsandsideeffects/treatmenttypes/photodynamictherapy.Html, accessed Aug. 3, 2017, last revised Mar. 18, 2015.*
Alegria. Journal of Photochemistry and Photobiology A: Chemistry, 2007, 185, 206-213).*
Jul. 18, 2017 Written Opinion of the International Searching Authority issued in International Patent Application No. PCT/CN2016/112586.
Jul. 18, 2017 International Search Report issued in International Patent Application No. PCT/CN2016/112586.
Gushchina, O.I. et al. "Synthesis of Amide Derivatives of Chlorin e6 and Investigation of their Biological Activity." Journal of Photochemistry & Photobiology, B:Biology, vol. 153, pp. 76-81, 2015.
Kwitniewski, Mateusz et al. "Diamino Acid Derivatives of PpIX as Potential Photosensitizers for Photodynamic Therapy of Squamous Cell Carcinoma and Prostate Cancer: In Vitro Studies." Journal of Photochemistry and Photobiology B:Biology, vol. 94, pp. 214-222, 2009.
Vaz Serra, V. et al. "New Porphyrin Amino Acid Conjugates: Synthesis and Photodynamic Effect in Human Epithelial Cells." Bioorganic & Medicinal Chemistry, vol. 18, pp. 6170-6178, 2010.
Jianzhong, Yao et al. "Synthesis and Photosensitizing Abilities as Well as Tumor Photobiological Activities of Chlorin F Methyl Ether" Acta Pharmaceutics Sinica, vol. 35(1): pp. 63-66, 2000.
Wang, H.M. et al. "Porphyrin with Amino Acid Moieties: A Tumor Photosensitizer." Chemico-Biological Interactions, vol. 172, pp. 154-158, 2008.
Pandey, Ravindra K. et al. "Chlorin and Porphyrin Derivatives as Potential Photosensitizers in Photodynamic Theraphy." Photochemistry and Photobiology, vol. 53, No. 1, pp. 65-72, 1991.
Guo, Xiuhan et al. "Syntheses of New Chlorin Derivatives Containing Maleimide Functional Group and Their Photodynamic Activity Evaluation." Bioorganic & Medicinal Chemistry Letters, vol. 25, pp. 4078-4081, 2015.
Waruna Jinadasa, R.G. et al. "Syntheses and Cellular Investigations of 173-, 152-, and 131-Amino Acid Derivatives of Chlorin e6." Journal of Medicinal Chemistry, vol. 54, pp. 7464-7476, 2011.

(Continued)

*Primary Examiner* — Noble E Jarrell
(74) *Attorney, Agent, or Firm* — Oliff PLC

(57) ABSTRACT

The present application relates to a new chlorin e6 derivatives and pharmaceutically acceptable salt thereof, as well as preparation and use thereof, which belongs to the medicine field. The chlorin e6 ether amino acid derivative comprises general structural formula I and optical isomers thereof. The preparation process comprises etherification of 3-vinyl in chlorin e6, A peptide is produced from 15-carboxylethyl and amino acid. The chlorin e6 ether amino acid derivative and pharmaceutically acceptable salt thereof can be used as a photodynamic anti-tumor drug. Compared with the prior similar photosensitizer Talaporfin used in clinic, the chlorin e6 ether amino acid derivative of the present application possess improved photodynamic anti-tumor activities and a high ratio of darktoxicity-phototoxicity. The prepared new photodynamic anti-tumor drugs comprises photodynamic anti-cancer drugs, drugs for photodynamic treatment of benign vascular diseases, such as age-related macular degeneration and naevus flammeus, and drugs for photodynamic treatment of condyloma acuminate.

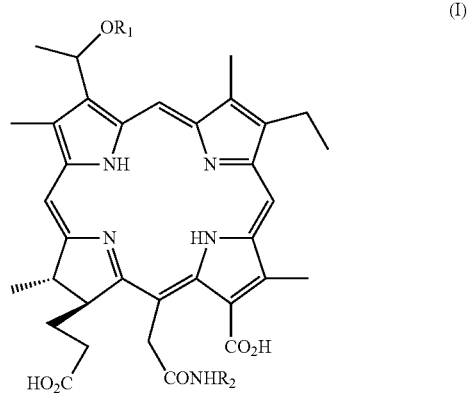

10 Claims, No Drawings

(56) References Cited

OTHER PUBLICATIONS

Zhu, Guo-hua et al. "Synthesis Procedure and Optical Quality of 132-N-(2-Hydroxyethyl)-153-N-(2-Hydroxyethyl)-17-3-Methoxycarbonyl-Chlorin-e6-13-1-15-2-Diamide and Optical Quality." Chemical Engineer, vol. 235, No. 4, pp. 1-5, 2015.
Fang, Yin et al. "Degradation of Silkworm Excrement Crude Chlorophyll and Synthesis of Chlorin e6 Ether Derivatives." Organic Chemistry, vol. 15, No. 5, pp. 493-498, 1995.
Ma, Fu-jia et al. "Optimization of Synthesis of Photosensitizer Chriorin e6 by Orthogonal Design." Chinese Journal of Pharmaceuticals, vol. 40, No. 20, pp. 1589-1591, 2005.

\* cited by examiner

CHLORIN E6 DERIVATIVE AND PHARMACEUTICALLY ACCEPTABLE SALT THEREOF AND PROCESS FOR PREPARING AND USE OF THE SAME

TECHNICAL FIELD

The present application relates to the medicine field, specifically to a new chlorin photosensitizer, chlorin e6 ether amino acid derivatives and pharmaceutically acceptable salt thereof, process for preparing and use in preparing anti-tumor drugs, etc.

BACKGROUND OF THE INVENTION

Photodynamic therapy (PDT) has developed into a new treatment for tumors since earlier 1980s. Its principle is to irradiate a focus (tumor) tissue into which a photosensitizer has been injected by laser of special wavelength. Elemental oxygen ($O_2$) existing in the tissue is excited by the photosensitizer to produce a reactive oxygen species (ROS), such as singlet oxygen ($^1O_2$). Thus, apoptosis or necrosis of tumor cells occurs and the tumor is treated. So called special wavelength means the largest absorption wavelength of the photosensitizer in the red region (>600 nm). PDT just specifically irradiates tumor tissues and selectively damages tumor cells, but with little or no damage to normal tissues or organs. It is a non invasive therapy for human body, with little side effect (no trauma and pains due to surgery, no emesis, nausea and immunosuppression due to radiotherapy and chemotherapy), and it can be used alone or combined with other therapies for many times.

Light, oxygen in tissues and photosensitizers are three main factors for PDT. Further, photosensitizers play a key role. The first generation of porphyrin photosensitizer, such as porfimer sodium is successfully used in tumor treatment in clinic, and a significant effect is achieved. However, there are some obvious defects, 1) a short of absorption wavelength (630 nm) in the red region causes the wavelength and matched laser cannot penetrate enough depth to skill tumor and a small molar absorption coefficient ($\epsilon$). Thus, photoactive activity is lower. 2) They are mixture of multicomponent porphyrin. 3) The elimination rate in vivo is slow and the retentive phototoxicity is large. After receiving the treatment, the patient needs to be protected from the light for 4-8 weeks. The patient feels great psychological pain. Therefore, since later 1990s, researchers have stated the studies on the second generation of photosensitizers represented by chlorin photosensitizers, such as benzoporphyrin derivatives (BPD), chlorophyll a degradation derivatives and bacteriochlorin. Since the structure of chlorins photosensitizer is clear and simple, the biggest absorption wavelength in the red region (>600 nm) is changed to 660-690 nm compared with the first generation of porphyrins photosensitizer, the laser of this wavelength possesses the best depth for tumor skilling. Further the molar absorption coefficient ($\epsilon$) of chlorins photosensitizer is higher than that of the first generation of porphyrins photosensitizer by one order of magnitude. The photoactive activity is strong, the metabolism in body is fast, and the retentive phototoxicity is small. It has been a hotspot in the research for new photosensitizers. The report regarding chlorins photosensitizer is increasing (for example, zhu guohua et. al., Synthetic process fro $13^2$-N-(2-hydroxyethyl)-$15^3$-N-(2-hydroxyethyl)-$17^3$-methoxycarbonyl chlorin e6-$13^1$,$15^2$-diamide and studies on optical property. Chemical Engineer, 2015, 235(4): 1-5; Fang ying, et al., The degradation of silkworm feces chlorophyll and Synthesis of chlorin e6 ether derivatives. organic chemistry, 1995, 15(5): 493-498; Xiuhan Guo, et al. Synthesis of new chlorin derivatives containing maleimide functional group and their photodynamic activity evaluation. Bioorganic & Medicinal Chemistry Letters, 2015, 25(19): 4078-4081; Gushchina, O. I., et al. Synthesis of amide derivatives of chlorine e6 and investigation of their biological activity. Journal of Photochemistry and Photobiology B: Biology, 2015, 153: 76-81; Kwitniewski, M., et al. Diamino acid derivatives of PpIX as potential photosensitizers for photodynamic therapy of squamous cell carcinoma and prostate cancer: in vitro studies. Journal of Photochemistry and Photobiology B: Biology, 2009, 94, 214-222; Serra, V. V., New porphyrin amino acid conjugates: synthesis and photodynamic effect in human epithelial cells. Bioorganic & Medicinal Chemistry, 2010, 18, 6170-6178; Wang, H. M., Porphyrin with amino acid moieties: a tumor photosensitizer. Chem. Biol. Interact. 2008, 172, 154-158; Smith, K. M., et al. Syntheses and cellular investigations of $17^3$-, $15^2$-, and $13^1$-amino acid derivatives of chlorin e6. Journal of Medicinal Chemistry, 2011, 54: 7464-7476; Yao jianzong, et al., Synthesis and photosensitizing abilities as well as tumor photobiological activities of Chlorin F methyl ether. Acta Pharmaceutica Sinica, 2000, 35(1): 63-66, 2001, 39(1): 1-4; Pandey, R. K., et al. Chlorin and porphyrin derivatives as potential photosensitizers in photodynamic therapy. Photochemistry and Photobiology, 1991, 53(1): 65-72). Although the potential effects of almost of optimized products are better, most of them have non-ideal activity data, higher toxicity, harder synthesis or lower yield. Thus, their use is hard to be achieved.

After 2000, some photosensitizers are successfully used in clinic, wherein verteporfiin comes into the market in 2000. Temoporfin comes into the market in 2001. Talaporfin comes into the market in 2004. In addition, phase I and II clinical test of pyropheophorbide a n-hexyl ether [HPPH, trade name: Photochlor] have been conducted by Hisun Pharmaceutical. It can be used for treating head and neck cancer. However, drugs for treating tumors are so less, patents have so little space to select them. Further, the treatment effects also need to be enhanced, and the toxicity might be reduced. Therefore, in the present application chlorin e6 is used as a raw material, its structure is modified and optimized to develop a new chlorins photosensitizer with a high effect and a low toxicity.

SUMMARY OF THE INVENTION

Regarding the defects in the art, the present application provides a new chlorin e6 derivative and pharmaceutically acceptable salt thereof, and the process and use of the same. The present application aims at finding a photodynamic anti-tumor drug with new structure, strong anti-tumor activity, lower toxicity and high treatment index.

The object of the present application is achieved by the following technical solutions.

A chlorin e6 derivative and pharmaceutically acceptable salt thereof is provided. The chlorin e6 derivative is a chlorin e6 ether amino acid derivative. The chlorin e6 ether amino acid derivative comprises general structural formula I and an optical isomer of general structural formula I,

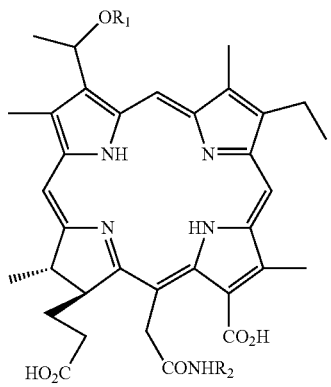

In the above general structural formula I, $R_1$ represents H, a lower alkyl, a higher alkyl, $(CH_2)_mOR_3$ or $(CH_2CH_2O)_kR_4$, wherein the higher alkyl is a linear or branched alkyl containing 7-18 carbon atoms, $R_3$ and $R_4$ independently represent H, a lower alkyl, m and k independently represent any integers between 2 and 6, in $R_1$, $R_3$ and $R_4$, the lower alkyl is a linear or branched alkyl containing 1-6 carbon atoms, $R_2$ represents an amino acid residue.

Further preferably, in general structural formula I, $R_1$ represents $CH_3$, $C_3H_7$, $C_6H_{13}$, $(CH_2)_2OCH_3$, $CH_2)_2OC_3H_7$, $(CH_2)_3OCH_3$, $(CH_2)_4OCH_3$, $(CH_2CH_2O)_2CH_3$ or $(CH_2CH_2O)_3CH_3$.

Further preferably, in general structural formula I, $R_2$ represents aspartic acid, glutamic acid or lysine residue.

Further preferably, regarding the structure of the chlorin e6 ether amino acid derivative and pharmaceutically acceptable salt thereof, the general structural formula I may be selected from any one of $I_1$-$I_{27}$, in $I_1$-$I_{27}$, the structure of $R_1$ and $R_2$ is shown as follows, respectively. That is, the preferable combination of $R_1$ and $R_2$ substitutes is shown in Table 1.

TABLE 1 part of preferable chlorin e6 ether amino acid derivatives $I_1$-$I_{27}$

| compound | $R_1$ | $R_2$ |
|---|---|---|
| $I_1$ | $CH_3$ | $CH(CO_2H)CH_2CO_2H$ |
| $I_2$ | n-$C_3H_7$ | $CH(CO_2H)CH_2CO_2H$ |
| $I_3$ | n-$C_6H_{13}$ | $CH(CO_2H)CH_2CO_2H$ |
| $I_4$ | $(CH_2)_2OCH_3$ | $CH(CO_2H)CH_2CO_2H$ |
| $I_5$ | $(CH_2)_2O$-n-$C_3H_7$ | $CH(CO_2H)CH_2CO_2H$ |
| $I_6$ | $(CH_2)_3OCH_3$ | $CH(CO_2H)CH_2CO_2H$ |
| $I_7$ | $(CH_2)_4OCH_3$ | $CH(CO_2H)CH_2CO_2H$ |
| $I_8$ | $(CH_2CH_2O)_2CH_3$ | $CH(CO_2H)CH_2CO_2H$ |
| $I_9$ | $(CH_2CH_2O)_3CH_3$ | $CH(CO_2H)CH_2CO_2H$ |

TABLE 1-continued part of preferable chlorin e6 ether amino acid derivatives $I_1$-$I_{27}$

| compound | $R_1$ | $R_2$ |
|---|---|---|
| $I_{10}$ | $CH_3$ | $CH(CO_2H)CH_2CH_2CO_2H$ |
| $I_{11}$ | n-$C_3H_7$ | $CH(CO_2H)CH_2CH_2CO_2H$ |
| $I_{12}$ | n-$C_6H_{13}$ | $CH(CO_2H)CH_2CH_2CO_2H$ |
| $I_{13}$ | $(CH_2)_2OCH_3$ | $CH(CO_2H)CH_2CH_2CO_2H$ |
| $I_{14}$ | $(CH_2)_2O$-n-$C_3H_7$ | $CH(CO_2H)CH_2CH_2CO_2H$ |
| $I_{15}$ | $(CH_2)_3OCH_3$ | $CH(CO_2H)CH_2CH_2CO_2H$ |
| $I_{16}$ | $(CH_2)_4OCH_3$ | $CH(CO_2H)CH_2CH_2CO_2H$ |
| $I_{17}$ | $(CH_2CH_2O)_2CH_3$ | $CH(CO_2H)CH_2CH_2CO_2H$ |
| $I_{18}$ | $(CH_2CH_2O)_3CH_3$ | $CH(CO_2H)CH_2CH_2CO_2H$ |
| $I_{19}$ | $CH_3$ | $CH(CO_2H)CH_2CH_2CH_2NH_2$ |
| $I_{20}$ | n-$C_3H_7$ | $CH(CO_2H)CH_2CH_2CH_2NH_2$ |
| $I_{21}$ | n-$C_6H_{13}$ | $CH(CO_2H)CH_2CH_2CH_2NH_2$ |
| $I_{22}$ | $(CH_2)_2OCH_3$ | $CH(CO_2H)CH_2CH_2CH_2NH_2$ |
| $I_{23}$ | $(CH_2)_2O$-n-$C_3H_7$ | $CH(CO_2H)CH_2CH_2CH_2NH_2$ |
| $I_{24}$ | $(CH_2)_3OCH_3$ | $CH(CO_2H)CH_2CH_2CH_2NH_2$ |
| $I_{25}$ | $(CH_2)_4OCH_3$ | $CH(CO_2H)CH_2CH_2CH_2NH_2$ |
| $I_{26}$ | $(CH_2CH_2O)_2CH_3$ | $CH(CO_2H)CH_2CH_2CH_2NH_2$ |
| $I_{27}$ | $(CH_2CH_2O)_3CH_3$ | $CH(CO_2H)CH_2CH_2CH_2NH_2$ | wherein, n represents "normal-".

Further, pharmaceutically acceptable salt of the chlorin e6 ether amino acid derivative is an inorganic alkali salt, preferably sodium salt of chlorin e6 ether amino acid derivative.

A process for preparing the chlorin e6 ether amino acid derivative is also provided, the process comprising:

S11: Chlorin e6 (chlorin e6, V) is used as a raw material. The chlorin e6 is commercially available. Alternatively, it can be synthesized by the method described in reference (Ma jiafu, Yao jianzong, et al., Optimization of synthetic process of photosensitizer chlorin e6 by orthogonal experiments. Chinese Journal of Pharmaceuticals, 2005, 40(20): 1589-1591.).

S12: Addition reaction is conducted between 3-vinyl of chlorin e6 and halogen hydride, then the addition product is aicoholized by an alcohol ($R_1$OH), S13: A peptide condensation reaction is conducted between 15-carboxylethyl in chlorin e6 and amino acid to result chlorin e5 ether amino acid derivative I.

Further preferably, in the step S13, 15-carboxylethyl in chlorin e6 is reacted with 1-(3-dimethylamino propyl)-3-ethyl carbodiimide hydrochloride (EDCl) and several carboxyl tert-butyl protected/non-α-amino t-butyloxycarboryl protected L-amino acid hydrochloride ($R_2'NH_2.HCl$) to produce carboxyl and amino protected chlorin e6 ether amino acid derivatives, then the carboxyl and amino protected chlorin e6 ether amino add derivatives off-protect tert-butyl/t-butyloxycarboryl to produce target compounds chlorin e6 ether amino acid derivatives.

Further preferably, the process for preparing the chlorin e6 ether amino acid derivative comprises:

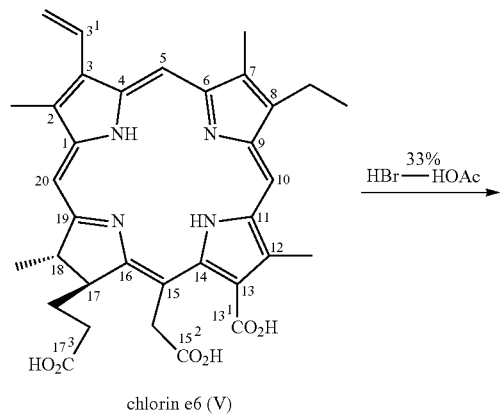

chlorin e6 (V)

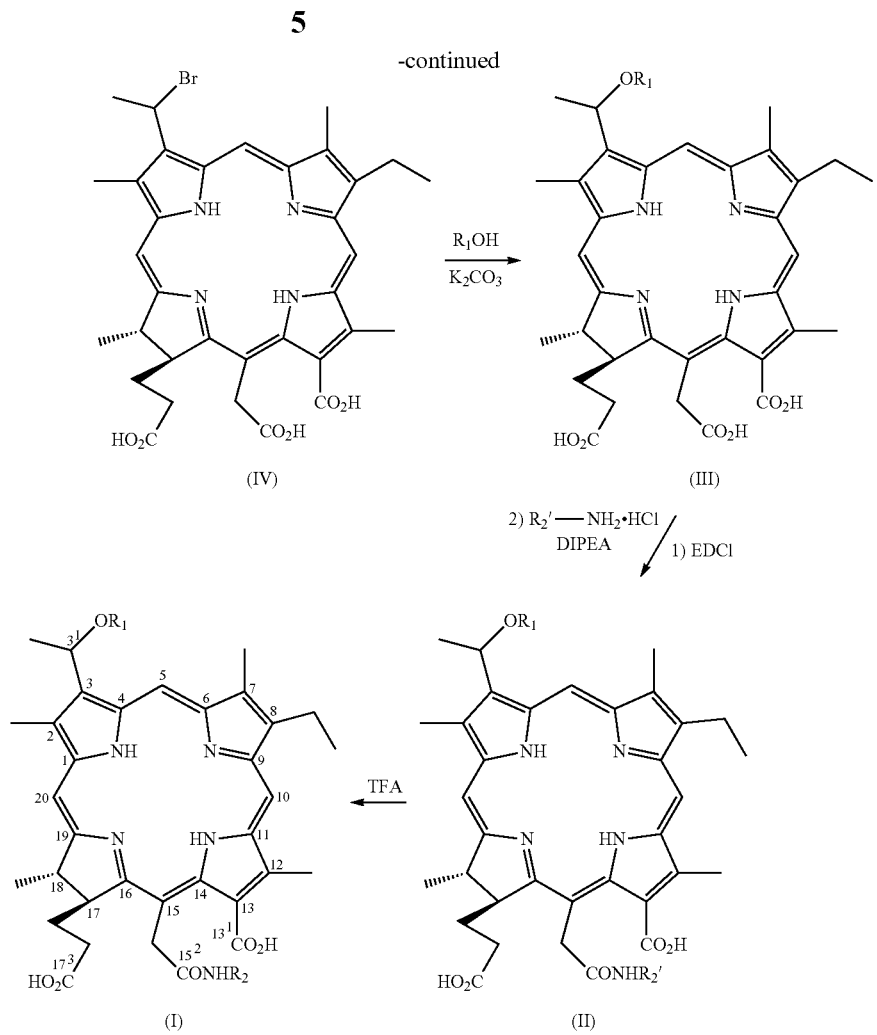

S1: chlorin e6 (V) is reacted with excess 33% HBr in glacial acetic acid at room temperature for 10-30 h to produce 3-(1-bromoethyl)-3-devinyl chlorin e6, ie., compound IV, S2: compound IV is reacted with an alcohol ($R_1OH$) in the presence of excess $K_2CO_3$ to produce compound III, S3: in dry or anhydrous N,N-dimethylformamide (DMF), compound III is reacted with 1-(3-dimethylamino propyl)-3-ethyl carbodiimide hydrochloride (EDCl) at room temperature for 2-6 h, then in the presence of N,N-dimethyl isopropyl amine (DIPEA) is reacted with various of carboxyl tert-butyl protected/non-α-amino t-butyloxycarboryl protected L-amino acid hydrochloride ($R_2'NH_2.HCl$) to produce carboxyl and amino protected chlorin e6 ether amino acid derivatives II, S4: compound II is off-protected of tert-butyl/t-butyloxycarboryl by trifluoroacetic acid (TFA) to produce target compound I, i.e., chlorin e6 ether amino acid derivative.

Further preferably, the above chlorin e6 can be prepared by chlorophyll a through acid or alkali degradation. The chlorophyll a can be chlorophyll a in silkworm feces or marine phytoplankton, for example, alga, such as *spirulina*.

The content of chlorophyll a in silkworm feces and *spirulina* is 0.75% and 1%-2%, respectively on the basis of their dry weight. Therefore, the both are abundant and cheap chlorophyll resource. Prepared chlorin e6 ether amino acid derivatives from silkworm feces or alga can extend the medicine use of silkworm feces or alga.

The process for preparing chlorin e6 (chlorin e6, V) using chlorophyll a (chlorophyll a, VII) as a raw material is provided as follows:

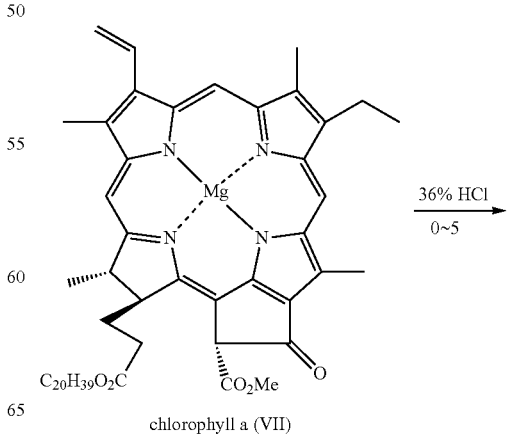

chlorophyll a (VII)

-continued

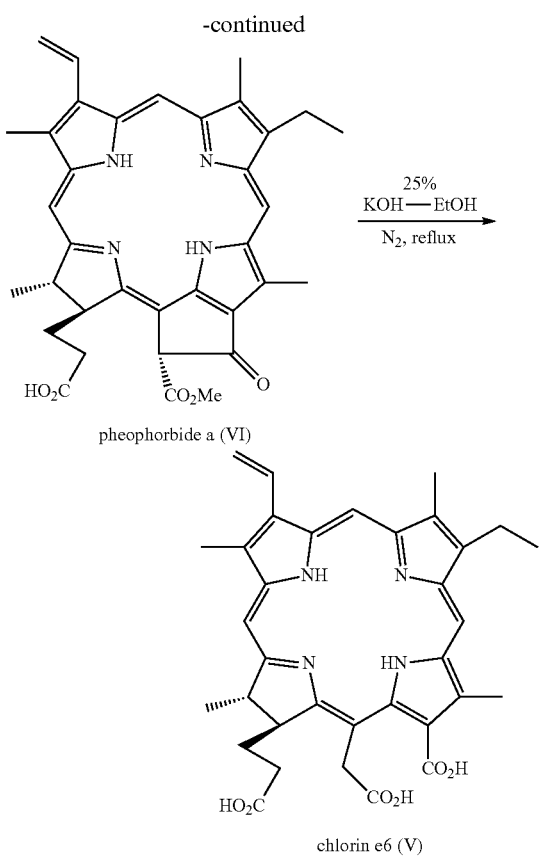

pheophorbide a (VI)

chlorin e6 (V)

a. chlorophyll a (pasty chlorophyll) crude extracts of commercially available silkworm feces or crude extracts of alga chlorophyll a in ethyl ether is reacted with equivalent volume of concentrated hydrochloric acid at 0-5° C. under stirring for 1 h to produce phoeophorbide a (pheophorbide a, VI);

b. compound VI is reacted with 25% potassium hydroxide in ethanol under refluxing, with nitrogen gas for 20 min to produce compound V.

Further, the process for preparing pharmaceutically acceptable salts of the chlorin e6 ether amino acid derivative comprises the chlorin e6 ether amino acid derivative is used to synthsize an inorganic alkali salt of chlorin e6 ether amino acid derivative. Specifically, chlorin e6 ether amino acid derivatives may be reacted with hydroxide of an inorganic alkali or an inorganic alkali to produce an inorganic alkali salt of chlorin e6 ether amino acid derivatives. For example, it can react with sodium hydroxide to produce a sodium salt.

Use of the chlorin e6 derivative and pharmaceutically acceptable salt thereof in preparing drugs for treating tumors is provided.

Use of the chlorin e6 derivative and pharmaceutically acceptable salt thereof in preparing drugs for treating benign vascular diseases is provided. The benign vascular diseases comprise macular degeneration and naevus flammeus.

Use of the chlorin e6 derivative and pharmaceutically acceptable salt thereof in preparing drugs for treating condyloma acuminata is provided.

The present application provides a chlorin e6 derivative and pharmaceutically acceptable salt thereof, a process for preparing the same and use thereof. The main advantageous effects are listed as follows.

a. A new chlorin e6 ether amino acid derivative is produced in the present application by optimizing the structure of chlorin e6, wherein 3-vinyl is etherified by alcohols and 15-carboxylethyl and amino acids produce a structure of a peptide. The etherification of 3-vinyl in chlorin e6 improves its treatment effects. Further, its toxicity is reduced by incorporating amino acids into 15-carboxylethyl. Specifically, the chlorin e6 ether amino acid derivative or its salt possess good photodynamic killing effect to human non-small cell lung cancer cell A549 and mice melanoma cell B16-F10. Its advantages are high effect and low toxicity, which demonstrates that compounds of the present application can be used for preparing new photodynamic anti-tumor drugs, etc.

Compared with the second generation of photosensitizer Talaporfin used in clinic, chlorin e6 ether amino acid derivative or its salt of the present application, the photodynamic anti-cancer activity is stronger and the ratio of darktoxicity-phototoxicity is higher. They can be used for preparing new photodynamic anti-cancer drugs, photodynamic drugs for treating benign vascular diseases, such as age-related macular degeneration (a proliferative disease of capillaries in retina) and naevus flammeus (a congenital abnormality of skin capillaries) and drugs for photodynamic treatment of condyloma acuminata (diseases infected by human papilloma virus).

b. The chlorin e6 ether amino acid derivative or its pharmaceutically acceptable salt of the present application is a new chlorins photosensitizer, with simple preparing processes, low toxicities, abundant raw materials, low device requirements and mild reaction condition, which can be applied in industry production expediently.

DETAILED DESCRIPTION OF THE INVENTION

The technical solutions of embodiments of the present application are described clearly and completely as follows. Obviously, the described embodiments are just some not all embodiments of the present application. The protection scope of the present application is not intended to be limited by embodiments of the present application provided below, but just represent selected embodiments of the present application. Based on embodiments of the present application, other embodiments that can be obtained by those skilled in the art without paying any creative work belong to the protection scope of the present application.

All reagents and raw material used in the present application are commercially available or prepared according to references. In the following embodiments, experiments without indicated specific conditions are conducted under the common conditions or those suggested by the manufactures.

Preparation of Chlorin e6 (V) from Chlorophyllin a (VII)

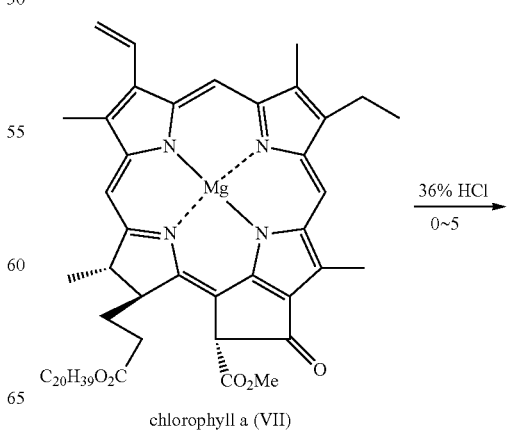

chlorophyll a (VII)

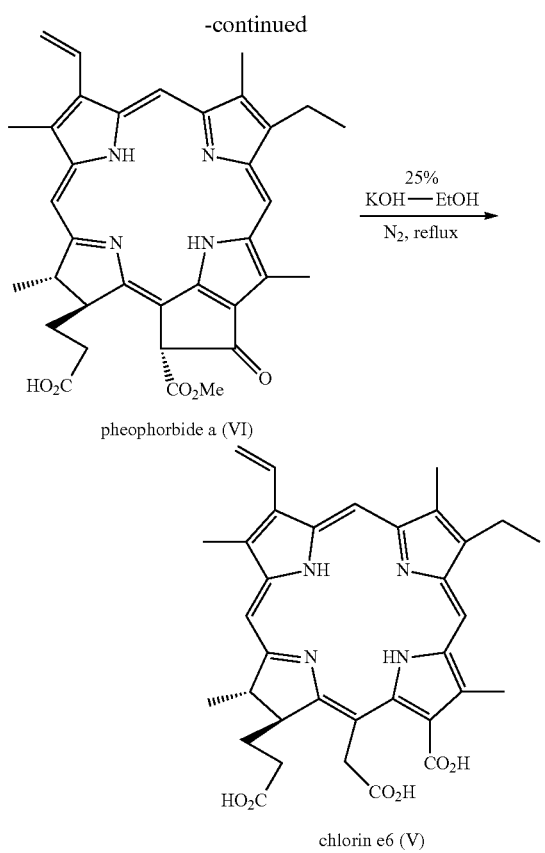

pheophorbide a (VI)

chlorin e6 (V)

100 g of crude extracts of silkworm feces chlorophyll a (VII) (Zhejiang Haining Fengming yelvesu Ltd) was dissolved in 500 mL of ethyl ether. Then, equivalent volume of concentrated hydrochloric acid was added at 0-5° C. and stirred for 1 h. Acid liquor was separated and extracted in the lower layer. 2 times of volume of water is added to dilute the acid liquor. The acid liquor is neutralized to a pH of 5-6 by 10 mol·L$^{-1}$ of NaOH. Then, suction filtering is conducted, and dried by $P_2O_5$ under vacuum to produce 15 g of black crude product powder of compound VI (the purity detected by HPLC normalization is 55%).

360 mL of 25% (w/v) potassium hydroxide in ethanol is added into the above crude product of compound VI (15 g, containing about 8.25 g of compound VI), refluxed under nitrogen gas for 20 min, stopping the reaction. The filtering was conducted. 2 times of water was added into filtrate for dilution. 10% of sulfuric acid were added for adjusting pH to 5-6, filtered, dried under vacuum by $P_2O_5$, separated by silica gel H column chromatography to produce 4.6 g of black powder, ie. chlorin e6 (V), with a yield of 55.4%.

The following Embodiments 1-27 are specific process for synthesizing target compound chlorin e6 ether amino acid derivatives (I) with different substitutes. The process is shown as follows:

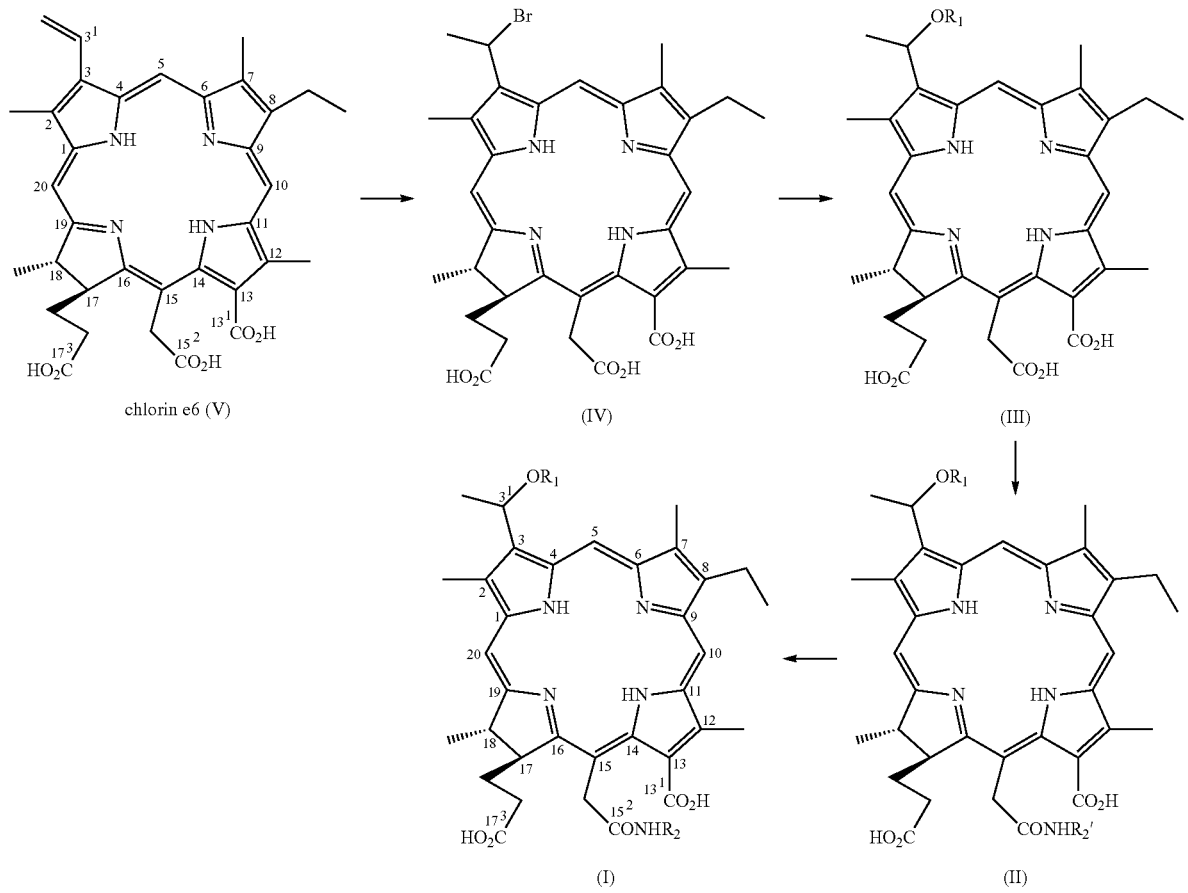

Embodiment 1: preparation of N-[3-(1-methoxy)ethyl-3-devinyl chlorin e6-15²-acyl]-L-aspartic acid ($I_1$)

S1: preparation of 3-(1-bromoethyl)-3-devinyl chlorin e6 (IV)

200 mL of 33/© HBr in glacial acetic acid at room temperature were added into compounds V (5.0 g), sealed and stirred for 24 h. Glacial acetic acid and excess HBr were vacuum evaporated to produce 5.6 g of deep green solid compound IV, ie. 3-(1-bromoethyl)-3-devinyl chlorin e6, without further purification before used in the next step of reaction.

S2: preparation of 3-(1-methoxy)ethyl-3-devinyl chlorin e6 ($III_1$)

Compound IV (1.12 g) was dissolved in 25 mL of anhydrous acetone. 2 g of $K_2CO_3$ and 2 mL of anhydrous methanol was added, refluxed under stirring for 2 h, and cooled to room temperature. 10 times of volume of water was added, excess $K_2CO_3$ was neutralized with 10% $H_2SO_4$ and adjusted pH to 5-6, filtered, dried under vacuum with $P_2O_5$, separated through silica gel H column chromatography to produce 0.58 g of black powder $III_1$, ie. 3-(1-methoxy)ethyl-3-devinyl chlorin e6, with a of yield 55.0%.

Chromatographic data of 3-(1-methoxy)ethyl-3-devinyl chlorin e6 ($III_1$) was MS (ESI$^+$) m/z: 629.72 [M+H]$^+$ (100%).

S3: preparation of N-[3-(1-methoxy)ethyl-3-devinyl chlorin e6-15²-acyl]-L-aspartic acid di-tert-butyl ester ($II_1$) production of Compound $III_1$ (135 mg, 0.215 mmol) was dissolved in 15 mL of anhydrous DMF. EDCl (42 mg, 0.215 mmol) was added at room temperature and reacted under stirring for 5 h. L-aspartic acid di-tert-butyl ester hydrochloride (73 mg, 0.258 mmol, 1.2 eq.) and DIPEA (86 μL, 0.516 mmol, 2.4 eq.) were added at room temperature and reacted under stirring. After the reaction completing as monitoring by TLC, 4 times of volume of $CH_2Cl_2$ was added for dilution. The reaction liquid was once washed with 5%© citric acid (weight percentage), 5% $NaHCO_3$ (mass concentration), water and saturated saline solution, respectively, dried with anhydrous $Na_2SO_4$. The solvents were recovered under a reduced pressure, and separated by chromatography to produce 130 mg of black powder $II_1$, with a yield of 70.7%.

Chromatographic data of N-[3-(1-methoxy)ethyl-3-devinyl chlorin e6-15²-acyl]-L-aspartic acid di-tert-butyl ester ($II_1$) was MS (ESI$^+$) m/z: 856.52 [M+H]$^+$ (100%).

S4: preparation of N-[3-(1-methoxy)ethyl-3-devinyl chlorin e6-15²-acyl]-L-aspartic acid Compound $II_1$ (50 mg, 0.0585 mmol) was dissolved in 5 mL anhydrous. $CH_2Cl_2$. 5 mL of trifluoroacetic acid (TFA) was added, and reacted under stirring in ice bath. After the reaction completing as monitoring by TLC, the solvents were recovered under a reduced pressure, and separated by chromatography to produce 36 mg of black powder $I_1$, with a yield of 82.9%.

Chromatographic data of N-[3-(1-methoxy)ethyl-3-devinyl chlorin e6-15²-acyl]-L-aspartic acid ($I_1$) was MS (ESI$^+$) m/z: 744.64 (M+H, 100%).

Embodiment 2: preparation of N-[3-(1-n-propoxyl)ethyl-3-devinyl chlorin e6-15²-acyl]-L-aspartic acid ($I_2$)

S1: process for preparing 3-(1-bromoethyl)-3-devinyl chlorin e6 (IV) was the same as step S1 of Embodiment 1.

S2: preparation of 3-(1-propoxyl)ethyl-3-devinyl chlorin e6 ($III_2$): according to step S2 in Embodiment 1, compound IV (1.12 g) was reacted with 2 mL of anhydrous n-propanol to produce 0.56 g of black solid $III_2$, yield 50.9%.

Chromatographic data of 3-(1-propoxyl)ethyl-3-devinyl chlorin e6 ($III_2$) was MS (ESI$^+$) m/z: 657.78 [M+H]$^+$ (100%).

S3: preparation of N-[3-(1-n-propoxyl)ethyl-3-devinyl chlorin e6-15²-acyl]-L-aspartic acid di-tert-butyl ester ($II_2$)

According to step S3 of Embodiment 1, compound $III_2$ (140 mg, 0.213 mmol) was reacted with the same equivalent EDCl, 1.2 times of equivalent L-aspartic acid di-tert-butyl ester hydrochloride and 2.4 times of equivalent DIPEA in anhydrous DMF to produce 125 mg of black powder $II_2$, with a yield of 66.3%.

Chromatographic data of N-[3-(1-n-propoxyl)ethyl-3-devinyl chlorin e6-15²-acyl]-L-aspartic acid di-tert-butyl ester ($II_2$) was MS (ESI$^+$) m/z: 884.63 [M+H]$^+$ (100%).

S4: preparation of N-[3-(1-n-propoxyl)ethyl-3-devinyl chlorin e6-15²-acyl]-L-aspartic acid ($I_2$)

According to step S4 of Embodiment 1, compound $II_2$ (50 mg, 0.0566 mmol) was reacted with $CH_2Cl_2$-TFA (1:1, v/v) to produce 35 mg of black powder $I_2$, with a yield of 80.2%.

Chromatographic data of N-[3-(1-n-propoxyl)ethyl-3-devinyl chlorin e6-15²-acyl]-L-aspartic acid ($I_2$) was MS (ESI$^+$) m/z: 772.66 [M+H]$^+$ (100%).

Embodiment 3: preparation of N-[3-(1-n-hexyloxy)ethyl-3-devinyl chlorin e6-15²-acyl]-L-aspartic acid ($I_3$)

S1: process for preparing 3-(1-bromoethyl)-3-devinyl chlorin e6 (IV) was the same as step S1 of Embodiment 1.

S2: preparation of 3-(1-n-hexyloxy)ethyl-3-devinyl chlorin e6 ($III_3$): according to step S2 in Embodiment 1, compound IV (1.12 g) was reacted with 2 mL of anhydrous hexyl alcohol to produce 0.48 g of black solid $III_3$, with a yield of 41.0%.

Chromatographic data of compound $III_3$ was MS (ESI$^+$) m/z: 699.68 [M+H]$^+$ 100%).

S3: preparation of N-[3-(1-n-hexyloxy)ethyl-3-devinyl chlorin e6-15²-acyl]-L-aspartic acid di-tert-butyl ester ($II_3$): according to step S3 of Embodiment 1, compound $III_3$ (150 mg, 0.215 mmol) was reacted with the same equivalent EDCl, 1.2 times of equivalent L-aspartic acid di-tert-butyl ester hydrochloride and 2.4 times of equivalent DIPEA in anhydrous DMF to produce 120 mg of black powder $II_3$, with a yield of 60.4%.

Chromatographic data of compound $II_3$ was: $^1$H NMR (600 MHz, $CD_3COCD_3$, δ, ppm): 10.01 (s, 1H), 9.87 (s, 1H), 9.05 (s, 1H), 7.09 (s, 1H), 6.09-6.03 (m, 1H), 5.50 (d, J=18.4 Hz, 1H), 5.41 (d, J=18.4 Hz, 1H), 4.70-4.66 (m, 2H), 4.63 (d, J=5.1 Hz, 1H), 3.85 (q, J=7.8 Hz, 2H), 3.77-3.72 (m, 1H), 3.65 (s, 3H), 3.64-3.59 (m, 1H), 3.50 (s, 3H), 3.32 (s, 3H), 2.78-2.63 (m, 4H), 2.39 (m, 2H), 2.11 (d, J=6.8 Hz, 3H), 1.77 (d, J=6.8 Hz, 3H), 1.73 (t, J=7.6 Hz, 3H), 1.28 (s, 9H), 1.25 (s, 9H), 1.16-1.12 (m, 6H), 0.74 (t, J=6.8 Hz, 3H), −1.37 (s, 1H), −1.58 (s, 1H), MS (ESI$^+$) m/z: 926.55 [M+H]$^+$ (100%).

S4: according to step S4 of Embodiment 1, compound $II_3$ (50 mg, 0.0541 mmol) was reacted with $CH_2Cl_2$-TFA (1:1, v/v) to produce 34 mg of black powder, ie., N-[3-(1-n-hexyloxy)ethyl-3-devinyl chlorin e6-15$^2$-acyl]-L-aspartic acid (I$_3$), with a yield of 77.4%.

Chromatographic data of compound I$_3$ was: UV-vis λ$_{max}$ (CH$_3$OH, nm) (ε/M$^{-1}$): 396 (89500), 497 (10200), 653 (36900), $^1$H NMR (600 MHz, CH$_3$OD, δ, ppm): 10.25 (s, 1H), 9.95 (s, 1H), 9.19 (s, 1H), 6.06-6.01 (m, 1H), 5.69 (d, J=18.5 Hz, 1H), 5.47 (d, J=18.5 Hz, 1H), 4.81-4.76 (m, 1H), 4.66-4.59 (m, 2H), 3.85 (q, J=7.7 Hz, 2H), 3.80-3.75 (m, 1H), 3.62 (s, 3H), 3.60-3.56 (m, 1H), 3.49 (s, 3H), 3.35 (d, J=4.6 Hz, 3H), 2.92 (s, 2H), 2.77-2.71 (m, 1H), 2.48-2.30 (m, 3H), 2.11 (d, I=6.8 Hz, 3H), 1.76 (d, =6.8 Hz, 3H), 1.67 (t, J=7.6 Hz, 3H), 1.22-1.08 (m, 6H), 0.70 (t, J=7.0 Hz, 3H), MS (ESI$^+$) m/z: 814.52 [M+H]$^+$ (100%), Embodiment 4: preparation of N-[3-[1-(2-methoxy)ethyoxyl]ethyl-3-devinyl chlorin e6-15$^2$-acyl]-L-aspartic acid di-tert-butyl ester (I$_8$)

S1: process for preparing 3-(1-bromoethyl)-3-devinyl chlorin e6 (IV) was the same as step S1 of Embodiment 1, S2: according to step S2 in Embodiment 1, compound IV (1.12 g) was reacted with 2 mL of anhydrous ethylene glycol monomethyl ether to produce 0.54 g of black solid 3-[1-(2-methoxy)ethyoxyl]ethyl-3-devinyl chlorin e6 (III$_4$), with a yield of 47.9%, Chromatographic data of compound III$_4$ was MS (Br) m/z: 673.72 [M+H]$^+$ (100%).

S3: according to step S3 of Embodiment 1, compound III$_4$ (150 mg, 0.223 mmol) was reacted with the same equivalent EDCl, 1.2 times of equivalent L-aspartic acid di-tert-butyl ester hydrochloride and 2.4 times of equivalent DIPEA in anhydrous DMF to produce 126 mg of black powder N-[3-[1-(2-methoxy)ethyoxyl]ethyl-3-devinyl chlorin e6-15$^2$-acyl]-L-aspartic acid di-tert-butyl ester (II$_4$), with a yield of 62.8%.

Chromatographic data of compound II$_4$ was MS (ESI$^+$) m/z: 900.54 [M+H]$^+$ (100%).

S4: according to step S4 of Embodiment 1, compound II$_4$ (50 mg, 0.0556 mmol) was reacted with CH$_2$Cl$_2$-TFA (1:1, v/v) to produce 35 mg of black powder N-[3-[1-(2-methoxy)ethyoxyl]ethyl-3-devinyl chlorin e6-15$^2$-acyl]-L-aspartic acid di-tert-butyl ester (I$_4$), with a yield of 80.0%, Chromatographic data of compound I$_4$ was: MS (ESI$^+$) m/z: 788.58 [M+H]$^+$ (100%).

Embodiment 5: preparation of N-[3-[1-(2-propoxyl)ethyoxyl]ethyl-3-devinyl chlorin e6-15$^2$-acyl]-L-aspartic acid (I$_5$)

S1: process for preparing 3-(1-bromoethyl)-3-devinyl chlorin e6 (IV) was the same as step S1 of Embodiment 1.

S2: according to step S2 in Embodiment 1, compound IV (1.12 g) was reacted with 2 mL of anhydrous ethylene glycol mono n-Propyl ether to produce 0.49 g of black solid 3-[1-(2-propoxyl)ethyoxyl]ethyl-3-devinyl chlorin e6 (III$_5$), with a yield of 41.7%.

Chromatographic data of compound III$_5$ was MS (ESI$^+$) m/z: 701.62 [M+H]$^+$ (100%).

S3: according to step S3 of Embodiment 1, compound III$_5$ (150 mg, 0.214 mmol) was reacted with the same equivalent EDCl, 1.2 times of equivalent L-aspartic acid di-tert-butyl ester hydrochloride and 2.4 times of equivalent DIPEA in anhydrous DMF to produce 110 mg of black powder N-[3-[1-(2-propoxyl)ethyoxyl]ethyl-3-devinyl chlorin e6-15$^2$-acyl]-L-aspartic acid di-tert-butyl ester (II$_5$), with a yield of 55.4%.

Chromatographic data of compound II$_5$ was $_{MS}$ (ESI$^+$) m/z: 928.68 [M+H]$^+$ (100%), S4: according to step S4 of Embodiment 1, compound II$_5$ (50 mg, 0.0539 mmol) was reacted with CH$_2$Cl$_2$-TFA (1:1, v/v) to produce 33 mg of black powder N-[3-[1-(2-propoxyl)ethyoxyl]ethyl-3-devinyl chlorin e6-15$^2$-acyl]-L-aspartic acid (I$_5$), with a yield of 75.1%.

Chromatographic data of compound I$_5$ was MS (ESI$^+$). m/z: 816.64 [M+H]$^+$ (100%).

Embodiment 6: preparation of N-[3-[1-(3-methoxy)propoxyl]ethyl-3-devinyl chlorin e6-15$^2$-acyl]-L-aspartic acid (I$_5$)

S1: process for preparing 3-(1-bromoethyl)-3-devinyl chlorin e6 (IV) was the same as step S1 of Embodiment 1.

S2: according to step S2 in Embodiment 1, compound IV (1.1.2 g) was reacted with 2 mL of anhydrous 1,3-propanediol monomethyl ether to produce 0.51 g of black solid 3-[1-(3-methoxy)propoxyl]ethyl-3-devinyl chlorin e6 (III$_6$), with a yield of 44.3%.

Chromatographic data of compound III$_6$ was: MS (ESI$^+$) m/z: 687.58 [M+H]$^+$ (100%).

S3: according to step S3 of Embodiment 1, compound III$_6$ (150 mg, 0.219 mmol) was reacted with the same equivalent EDCl, 1.2 times of equivalent L-aspartic acid di-tert-butyl ester hydrochloride and 2.4 times of equivalent DIPEA in anhydrous DMF to produce black powder N-[3-[1-(3-methoxy)propoxyl]ethyl-3-devinyl chlorin e6-15$^2$-acyl]-L-aspartic acid di-tert-butyl ester (II$_6$) 115 mg, with a yield of 57.6%.

Chromatographic data of compound II$_6$ was MS (ESI$^+$) m/z: 914.58 [M+H]$^+$ (100%)

S4: according to step S4 of Embodiment 1, compound II$_6$ (50 mg, 0.0548 mmol) was reacted with CH$_2$Cl$_2$-TFA (1:1, v/v) to produce 34 mg of black powder N-[3-[1-(3-methoxy)propoxyl]ethyl-3-devinyl chlorin e6-15$^2$-acyl]-L-aspartic acid (I$_6$), with a yield of 77.5%.

Chromatographic data of compound I$_6$ was MS (Br) m/z: 802.62 [M+H]$^+$ (100%).

Embodiment 7: preparation of N-[3-[1-(4-methoxy)butoxy]ethyl-3-devinyl chlorin e6-15$^2$-acyl]-1-aspartic acid (I$_7$)

S1: process for preparing 3-(1-bromoethyl)-3-devinyl chlorin e6 (IV) was the same as step S1 of Embodiment 1.

S2: according to step S2 in Embodiment 1, compound IV (1.12 g) was reacted with 2 mL anhydrous 1,4-butanediol monomethyl ether to produce 0.47 g of black solid 3-[1-(4-methoxy)butoxy]ethyl-3-devinyl chlorin e6 (III$_7$), with a yield of 40.0%.

Chromatographic data of compound III$_7$ was MS (ESI$^+$) m/z: 701.62 [M+H]$^+$ (100%).

S3: according to step S3 of Embodiment 1, compound III$_7$ (150 mg, 0.214 mmol) was reacted with the same equivalent EDCl, 1.2 times of equivalent L-aspartic acid di-tert-butyl ester hydrochloride and 2.4 times of equivalent DIPEA in anhydrous DMF to produce 112 mg of black powder N-[3-[1-(4-methoxy)butoxy]ethyl-3-devinyl chlorin e6-15$^2$-acyl]-L-aspartic acid di-tert-butyl ester (II$_7$), with a yield 56.4%.

Chromatographic data of compound II$_7$ was MS (ESI$^+$) m/z: 928.66 [M+H]$^+$ (100%).

S4: according to step S4 of Embodiment 1, compound II$_7$ (50 mg, 0.0539 mmol) was reacted with CH$_2$Cl$_2$-TFA (1:1, v/v) to produce 32 mg of black powder N-[3-[1-(4-methoxy) butoxy]ethyl-3-devinyl chlorin e6-15$^2$-acyl]-L-aspartic acid ($I_7$), with a yield of 72.8%.

Chromatographic data of compound $I_7$ was MS (ESI$^+$) m/z: 816.52 [M+H]$^+$ (100%).

Embodiment 8: preparation of N-[3-[1-(2-(2-methoxy)ethyoxyl)ethyoxyl]ethyl-3-devinyl chlorin e6-15$^2$-acyl]-L-aspartic acid ($I_8$)

S1: process for preparing 3-(1-bromoethyl)-3-devinyl chlorin e6 (IV) was the same as step S1 of Embodiment 1.

S2: according to step S2 in Embodiment 1, compound IV (1.12 g) was reacted with 2 mL of anhydrous diethylene glycol monomethyl ether to produce 0.49 g of black solid 3-[1-(2-(2-methoxy)ethyoxyl)ethyoxyl]ethyl-3-devinyl chlorin e6 ($III_8$), with a yield of 40.7%.

Chromatographic data of compound $III_8$ as MS (ESI$^+$) m/z: 717.59 [M+H]$^+$ (100%).

S3: according to step S3 of Embodiment 1, compound $III_8$ (150 mg, 0.209 mmol) was reacted with the same equivalent EDCl, 1.2 times of equivalent L-aspartic acid di-tert-butyl ester hydrochloride and 2.4 times of equivalent DIPEA in anhydrous DMF to produce 100 mg of black powder N-[3-[1-(2-(2-methoxy)ethyoxyl)ethyoxyl]ethyl-3-devinyl chlorin e6-15$^2$-acyl]-L-aspartic acid di-tert-butyl ester ($II_8$), with a, yield of 50.6%.

Chromatographic data of compound $II_8$ was MS (ESI$^+$) m/z: 944.52 [M+H]$^+$ (100%).

S4: according to step S4 of Embodiment 1, compound $II_8$ (50 mg, 0.0530 mmol) was reacted with CH$_2$Cl$_2$-TFA (1:1, v/v) to produce 30 mg of black powder N-[3-[1-(2-(2-methoxy)ethyoxyl)ethyoxyl]ethyl-3-devinyl chlorin e6-15$^2$-acyl]-L-aspartic acid ($I_8$), with a yield of 68.1%.

Chromatographic data of compound $I_8$ was MS (ESI$^+$) m/z: 832.60 [M+H]$^+$ (100%).

Embodiment 9: preparation of N-[3-[1-(2-(2-(2-methoxy)ethyoxyl)ethyoxyl) ethyoxyl]ethyl-3-devinyl chlorin e6-15$^2$-acyl]-L-aspartic acid ($I_9$)

S1: process for preparing 3-(1-bromoethyl)-3-devinyl chlorin e6 (IV) was the same as step S1 of Embodiment 1.

S2: according to step S2 in Embodiment 1, compound IV (1.12 g) was reacted with 2 mL of anhydrous triethylene glycol monomethyl ether to produce 0.42 g of black solid 3-[1-(2-(2-(2-methoxy)ethyoxyl)ethyoxyl) ethyoxyl]ethyl-3-devinyl chlorin e6 ($III_9$), with a yield of 33.1%.

Chromatographic data of compound $III_9$ was MS (ESI$^+$) m/z: 761.66 [M+H]$^+$ (100%)

S3: according to step S3 of Embodiment 1, compound $III_9$ (150 mg, 0.197 mmol) was reacted with the same equivalent EDCl, 1.2 times of equivalent L-aspartic acid di-tert-butyl ester hydrochloride and 2.4 times of equivalent DIPEA in anhydrous DMF to produce 90 mg of black powder N-[3-[1-(2-(2-(2-methoxy)ethyoxyl)ethyoxyl) ethyoxyl]ethyl-3-devinyl chlorin e6-15$^2$-acyl]-L-aspartic acid di-tert-butyl ester ($II_9$), with a yield of 46.2%.

Chromatographic data of compound $II_9$ was MS (ESI$^+$) m/z: 988.64 [M+H]$^+$ (100%).

S4: according to step S4 of Embodiment 1, compound $II_9$ (50 mg, 0.0507 mmol) was reacted with CH$_2$Cl$_2$-TFA (1:1, v/v) to produce 30 mg of black powder N-[3-[1-(2-(2-(2-methoxy)ethyoxyl) ethyoxyl)ethyoxyl]ethyl-3-devinyl chlorin e6-15$^2$-acyl]-L-aspartic acid ($I_9$), with a yield of 67.7%.

Chromatographic data of compound $I_9$ was MS (ESI$^+$) m/z: 876.68 [M+H]$^+$ (100%).

Embodiment 10: preparation of N-[3-(1-methoxy) ethyl-3-devinyl chlorin e6-15$^2$-acyl]-L-glutamic acid ($I_{10}$)

S1: process for preparing 3-(1-bromoethyl)-3-devinyl chlorin e6 (IV) was the same as step S1 of Embodiment 1.

S2: compound $III_1$ was prepared according to the same step S2 of Embodiment 1.

S3: according to step S3 of Embodiment 1, compound $III_1$ (150 mg, 0.239 mmol) was reacted with the same equivalent EDCl, 1.2 times of equivalent L-glutamic acid di-tert-butyl ester hydrochloride and 2.4 times of equivalent DIPEA in anhydrous DMF to produce 135 mg of black powder N-[3-(1-methoxy)ethyl-3-devinyl chlorin e6-15$^2$-acyl]-L-glutamic acid di-tert-butyl ester ($II_{10}$), with a yield of 65.0%©.

Chromatographic data of compound $II_{10}$ was MS (ESI$^r$) m/z: 870.58 [M+H]$^+$ (100%).

S4: according to step S4 of Embodiment 1, compound $II_{10}$ (50 mg, 0.0575 mmol) was reacted with CH$_2$Cl$_2$-TFA (1:1, v/v) to produce 38 mg of black powder N-[3-(1-methoxy) ethyl-3-devinyl chlorin e6-15$^2$-acyl]-L-glutamic acid ($I_{10}$), with a yield of 87.2%.

Chromatographic data of compound $I_{10}$ was MS (ESI$^+$) m/z: 758.55 [M+H]$^+$ (100%).

Embodiment 11: preparation of N-[3-(1-n-propoxyl) ethyl-3-devinyl chlorin e6-15$^2$-acyl]-L-glutamic acid ($I_{11}$)

S1: process for preparing 3-(1-bromoethyl)-3-devinyl chlorin e6 (IV) was the same as step S1 of Embodiment 1.

S2: process for preparing compound $III_7$ was the same as step S2 of Embodiment 2.

S3: according to step S3 of Embodiment 1, compound $III_7$ (150 mg, 0.229 mmol) was reacted with the same equivalent EDCl, 1.2 times of equivalent L-glutamic acid di-tert-butyl ester hydrochloride and 2.4 times of equivalent DIPEA in anhydrous DMF to produce 126 mg of black powder N-[3-(1-n-propoxyl)ethyl-3-devinyl chlorin e6-15$^2$-acyl]-L-glutamic acid di-tert-butyl ester (with a yield of 61.4%.

Chromatographic data of compound $II_{11}$ was MS (ESI$^+$) m/z: 898.62 [M+H]$^+$ (100%).

S4: according to step S4 of Embodiment 1, compound $II_{11}$ (50 mg, 0.0557 mmol) was reacted with CH$_2$Cl$_2$-TFA (1:1, v/v) to produce 36 mg of black powder N-[3-(1-n-propoxyl) ethyl-3-devinyl chlorin e6-15$^2$-acyl]-L-glutamic acid ($I_{11}$), with a yield of 823%.

Chromatographic data of compound $I_{11}$ was MS (ESI$^+$) m/z: 786.57 [M+H]$^+$ (100%).

Embodiment 12: preparation of N-[3-(1-n-hexyloxy)ethyl-3-devinyl chlorin e6-15$^2$-acyl]-L-glutamic acid ($I_{11}$)

S1: process for preparing 3-(1-bromoethyl)-3-devinyl chlorin e6 (IV) was the same as step S1 of Embodiment 1.

S2: process for preparing compound $III_3$, was the same as step S2 of Embodiment 3.

S3: according to step S3 of Embodiment 1, compound $III_3$ (150 mg, 0.215 mmol) was reacted with the same equivalent EDCl, 1.2 times of equivalent L-glutamic acid di-tert-butyl ester hydrochloride and 2.4 times of equivalent DIPEA in anhydrous DMF to produce 117 mg of black powder N-[3-

(1-n-hexyloxy)ethyl-3-devinyl chlorin e6-15²-acyl]-L-glutamic acid di-tert-butyl ester (II$_{12}$), with a yield of 58.0%.

Chromatographic data of compound II$_{12}$ was: $^1$H NMR (600 MHz, CD$_3$COCD$_3$, δ, ppm): 10.02 (s, 1H), 9.88 (s, 1H), 9.05 (s, 1H), 7.15 (s, 1H), 6.07 (m, 1H), 5.52 (d, J=18.4 Hz, 1H), 5.39 (d, J=18.4 Hz, 1H), 4.72-4.62 (m, 2H), 4.43-4.37 (m, 1H), 3.85 (q, J=7.8 Hz, 2H), 3.7-3.71 (m, 1H), 3.66 (s, 3H), 3.66-3.59 (m, 1H), 3.50 (s, 3H), 3.32 (s, 3H), 2.81-2.70 (m, 2H), 2.46-2.25 (m, 4H), 2.11 (d, J=6.6 Hz, 3H), 1.76 (d, J=7.0 Hz, 3H), 1.73 (t, J=7.5 Hz, 3H), 1.34 (s, 9H), 1.25-1.18 (m, 15H), 0.74 (t, J=6.4 Hz, 3H), −1.39 (s, 1H), −1.60 (s, 1H). MS (ESI$^+$) m/z: 940.72 [M+H]$^+$ (100%).

S4: according to step S4 of Embodiment 1, compound II$_{12}$ (50 mg, 0.0532 mmol) was reacted with CH$_2$Cl$_2$-TFA (1:1, v/v) to produce 35 mg of black powder N-[3-(1-n-hexyloxy) ethyl-3-devinyl chlorin e6-15²-acyl]-L-glutamic acid (I$_{12}$), with a yield of 79.5%.

Chromatographic data of compound I$_{11}$ was: UV-vis λ$_{max}$ (CH$_3$OH, nm) (ε/M$^{-1}$ cm$^{-1}$): 397 (87100), 497 (9200), 653 (33100). $^1$H NMR (600 MHz, CH$_3$OD, δ, ppm): 10.30 (s, 1H), 9.95 (s, 1H), 9.26 (s, 1H), 6.04-5.98 (m, 1H), 5.73 (d, J=17.7 Hz, 1H), 5.45 (d, J=17.7 Hz, 1H), 4.67-4.62 (m, 2H), 4.50-4.47 (m, 1H), 3.81-3.73 (m, 3H), 3.59 (s, 3H), 3.57-3.55 (m, 1H), 3.48 (s, 3H), 3.30 (s, 3H), 2.76-2.70 (m, 1H), 2.45-2.28 (m, 3H), 2.28-2.17 (m, 2H), 2.07 (d, J=6.7 Hz, 3H), 1.76 (d, 3H), 1.60 (t, J=7.6 Hz, 3H), 1.20-1.03 (m, 6H), 0.69 (t, J=7.0 Hz, 3H). MS (ESI$^+$) m/z: 828.62 [M+H]$^+$ (100%).

Embodiment 13: preparation of N-[3-[1-(2-methoxy)ethyoxyl]ethyl-3-devinyl chlorin e6-15²-acyl]-L-glutamic acid (I$_{13}$)

S1: process for preparing 3-(1-bromoethyl)-3-devinyl chlorin e6 (IV) was the same as step S1 of Embodiment 1.

S2: process for preparing compound III$_4$ was the same as step S2 of Embodiment 4.

S3: according to step S3 of Embodiment 1, compound III$_4$ (150 mg, 0.223 mmol) was reacted with the same equivalent EDCl, 1.2 times of equivalent L-glutamic acid di-tert-butyl ester hydrochloride and 2.4 times of equivalent DIPEA in anhydrous DMF to produce 120 mg of black powder N-[3-[1-(2-methoxy)ethyoxyl]ethyl-3-devinyl chlorin e6-15²-acyl]-L-glutamic acid di-tert-butyl ester (II$_{13}$), with a yield of 58.9%.

Chromatographic data of compound II$_{13}$ was MS (ESI$^+$) m/z: 914.56 [M+H]$^+$ (100%).

S4: according to step S4 of Embodiment 1, compound II$_{13}$ (50 mg, 0.0548 mmol) was reacted with CH$_2$Cl$_2$-TFA (1:1, v/v) to produce 34 mg of black powder N-[3-[1-(2-methoxy) ethyoxyl]ethyl-3-devinyl chlorin e6-15²-acyl]-L-glutamic acid (I$_{13}$), with a yield of 77.5%.

Chromatographic data of compound I$_{13}$ was MS (ESI$^+$) m/z: 802.65 [M+H]$^+$ (100%).

Embodiment 14: preparation of N-[3-[1-(2-propoxyl)ethyoxyl]ethyl-3-devinyl chlorin e6-15²-acyl]-L-glutamic acid (I$_{14}$)

S1: process for preparing 3-(1-bromoethyl)-devinyl chlorin e6 (IV) was the same as step S1 of Embodiment 1.

S2: process for preparing compound III$_5$ was the same as step S2 of Embodiment 5.

S3: according to step S3 of Embodiment 1, compound III$_5$ (150 mg, 0.214 mmol) was reacted with the same equivalent EDCl, 1.2 times of equivalent L-glutamic acid di-tert-butyl ester hydrochloride and 2.4 times of equivalent DIPEA in anhydrous DMF to produce 102 mg of black powder N-[3-[1-(2-propoxyl)ethyoxyl]ethyl-3-devinyl chlorin e6-15²-acyl]-L-glutamic acid di-tert-butyl ester (II$_{14}$), with a yield of 50.6%.

Chromatographic data of compound II$_{14}$ was MS (ESI$^+$) m/z: 942.66 [M+H]$^+$ (100%).

S4: according to step S4 of Embodiment 1, compound II$_{14}$ (50 mg, 0.0531 mmol) was reacted with CH$_2$Cl$_2$-TFA (1:1, v/v) to produce 32 mg of black powder N-[3-[1-(2-propoxyl] ethyoxyl]ethyl-3-devinyl chlorin e6-15²-acyl)-L-glutamic acid (I$_{14}$), with a yield of 72.6%.

Chromatographic data of compound I$_{14}$ was MS (ESI$^+$) m/z: 830.62 [M+H]$^+$ (100%).

Embodiment 15: preparation of N-[3-[1-(3-methoxy)propoxyl]ethyl-3-devinyl chlorin e6-15²-acyl]-L-glutamic acid (I$_{15}$)

S1: process for preparing 3-(1-bromoethyl)-3-devinyl chlorin e6 (IV) was the same as step S1 of Embodiment 1.

S2: process for preparing compound III$_6$ was the same as step S2 of Embodiment 6.

S3: according to step S3 of Embodiment 1, compound III$_6$ (150 mg, 0.219 mmol) was reacted with the same equivalent EDCl, 1.2 times of equivalent L-glutamic acid di-tert-butyl ester hydrochloride and 2.4 times of equivalent DIPEA in anhydrous DMF to produce 107 mg of black powder N-[3-[1-(3-methoxy)propoxyl]ethyl-3-devinyl chlorin e6-15²-acyl]-L-glutamic acid di-tert-butyl ester (II$_{15}$), with a yield of 52.8%.

Chromatographic data of compound II$_{15}$ was MS (ESI$^+$) m/z: 928.62 [M+H]$^+$ (100%).

S4: according to step S4 of Embodiment 1, compound II$_{15}$ (50 mg, 0.0539 mmol) was reacted with CH$_2$Cl$_2$-TFA (1:1, v/v) to produce 33 mg of black powder N-[3-[1-(3-methoxy) propoxyl]ethyl-3-devinyl chlorin e6-15²-acyl]-L-glutamic acid (I$_{11}$), with a yield of 75.1%.

Chromatographic data of compound I$_{15}$ was MS (ESI$^+$) m/z: 816.71 [M+H]$^+$ (100%).

Embodiment 16: preparation of N-[3-[1-(4-methoxy)butoxy]ethyl-3-devinyl chlorin e6-15²-acyl]-L-glutamic acid di-tert-butyl ester (I$_{16}$)

S1: process for preparing 3-(1-bromoethyl)-3-devinyl chlorin e6 (IV) was the same as step S1 of Embodiment 1.

S2: process for preparing compound III$_7$ was the same as step S2 of Embodiment 7.

S3: according to step S3 of Embodiment 1, compound III$_7$ (150 mg, 0214 mmol) was reacted with the same equivalent EDCl, 1.2 times of equivalent L-glutamic acid di-tert-butyl ester hydrochloride and 2.4 times of equivalent DIPEA in anhydrous DMF to produce 103 mg of black powder N-[3-[1-(4-methoxy)butoxy]ethyl-3-devinyl chlorin e6-15²-acyl]-L-glutamic acid di-tert-butyl ester (II$_{16}$), with a yield of 51.1%.

Chromatographic data of compound II$_{16}$ was MS (Br) m/z: 942.68 [M+H]$^+$ (100%).

S4: according to step S4 of Embodiment 1, compound II$_{16}$ (50 mg, 0.0531 mmol) was reacted with CH$_2$Cl$_2$-TFA (1:1, v/v) to produce 31 mg of black powder N-[3-[1-(4-methoxy) butoxy]ethyl-3-devinyl chlorin e6-15²-acyl]-L-glutamic acid di-tert-butyl ester (I$_{16}$), with a yield of 70.4%.

Chromatographic data of compound was MS (ESI$^+$) m/z: 830.59 [M+H]$^+$ (100%).

Embodiment 17: preparation of N-[3-[1-(2-(2-methoxy)ethyoxyl)ethyoxyl]ethyl-3-devinyl chlorin e6-15$^2$-acyl]-L-glutamic acid ($I_{17}$)

S1: process for preparing 3-(1-bromoethyl)-3-devinyl chlorin e6 (IV) was the same as step S1 of Embodiment 1, S2: process for preparing compound $III_8$ was the same as step S2 of Embodiment 8.

S3: according to step S3 of Embodiment 1, compound $III_8$ (150 mg, 0.209 mmol) was reacted with the same equivalent EDCl, 1.2 times of equivalent L-glutamic acid di-tert-butyl ester hydrochloride and 2.4 times of equivalent DIPEA in anhydrous DMF to produce 93 mg of black powder N-[3-[1-(2-(2-methoxy)ethyoxyl)ethyoxyl]ethyl-3-devinyl chlorin e6-15$^2$-acyl]-L-glutamic acid di-tert-butyl ester ($II_{17}$), with a yield of 46.4%.

Chromatographic data of compound $II_{17}$ was MS (ESI$^+$) m/z: 958.54 [M+H]$^+$ (100%).

S4: according to step S4 of Embodiment 1, compound $II_{17}$ (50 mg, 0.0522 mmol) was reacted with CH$_2$Cl$_2$-TFA (1:1, v/v) to produce 30 mg of black powder N-[3-[1-(2-(2-methoxy)ethyoxyl)ethyoxyl]ethyl-3-devinyl chlorin e6-15$^2$-acyl]-L-glutamic acid ($I_{17}$), with a yield of 68.0%.

Chromatographic data of compound $I_{17}$ was MS (ESI$^+$) m/z: 846.74 [M+H]$^+$ (100%).

Embodiment 18: preparation of N-[3-[1-(2-(2-(2-methoxy)ethyoxyl)ethyoxyl)ethyoxyl]ethyl-3-devinyl chlorin e6-15$^2$-acyl]-L-glutamic acid ($I_{18}$)

S1: process for preparing 3-(1-bromoethyl)-3-devinyl chlorin e6 (IV) was the same as step S1 of Embodiment 1.

S2: process for preparing compound $III_9$ was the same as step S2 of Embodiment 9.

S3: according to step S3 of Embodiment 1, compound $III_9$ (150 mg, 0.197 mmol) was reacted with the same equivalent EDCl, 1.2 times of equivalent L-glutamic acid di-tert-butyl ester hydrochloride and 2.4 times of equivalent DIPEA in anhydrous DMF to produce 85 mg of black powder N-[3-[1-(2-(2-(2-methoxy)ethyoxyl)ethyoxyl) ethyoxyl]ethyl-3-devinyl chlorin e6-15$^2$-acyl]l-glutamic acid di-tert-butyl ester ($II_{18}$), with a yield of 43.0%.

Chromatographic data of compound $II_{18}$ was MS (ESI$^+$) m/z: 1002.72 [M+H]$^+$ (100%).

S4: according to step S4 of Embodiment 1, compound $II_{18}$ (50 mg, 0.050 mmol) was reacted with CH$_2$Cl$_2$-TFA (1:1, v/v) to produce 30 mg of black powder N-[3-[1-(2-(2-(2-methoxy)ethyoxyl)ethyoxyl)ethyoxyl]ethyl-3-devinyl chlorin e6-15$^2$-acyl]-L-glutamic acid ($I_{18}$), with a yield of 67.6%.

Chromatographic data of compound $I_{18}$ was MS (ESI$^+$) m/z: 890.68 [M+H]$^+$ (100%).

Embodiment 19: preparation of N$^\alpha$-[3-(1-methoxy)ethyl-3-devinyl chlorin e6-15$^2$-acyl]-L-lysine ($I_{19}$)

S1: process for preparing 3-(1-bromoethyl)-3-devinyl chlorin e6 (IV) was the same as step S1 of Embodiment 1.

S2: process for preparing compound $III_1$ was the same as step S2 of Embodiment 1.

S3: according to step S3 of Embodiment 1, compound $III_1$ (150 mg, 0.239 mmol) was reacted with the same equivalent EDCl, 1.2 times of equivalent N$^\epsilon$-t-butyloxycarboryl-L-lysine tert-butyl ester hydrochloride and 2.4 times of equivalent DIPEA in anhydrous DMF to produce 138 mg of black powder N$^\alpha$-[3-(1-methoxy)ethyl-3-devinyl chlorin e6-15$^2$-acyl]-N$^\epsilon$-t-butyloxycarboryl-L-lysine tert-butyl ester ($II_{19}$), with a yield of 63.4%.

Chromatographic data of compound $I_{19}$ was MS (ESI$^+$) m/z: 913.56 [M+H]+(100%).

S4: according to step S4 of Embodiment 1, compound $II_{19}$ (50 mg, 0.0548 mmol) was reacted with CH$_2$Cl$_2$-TFA (1:1, v/v) to produce 33 mg of black powder N$^\alpha$-[3-(1-methoxy) ethyl-3-devinyl chlorin e6-15$^2$-acyl]-L-lysine ($I_{19}$), with a yield of 79.6%.

Chromatographic data of compound $I_{19}$ was MS (ESI$^+$) m/z: 757.58 [M+H]$^-$ (100%).

Embodiment 20: preparation of N-[3-(1-n-propoxyl) ethyl-3-devinyl chlorin e6-15$^2$-acyl]-L-lysine ($I_{20}$)

S1: process for preparing 3-(1-bromoethyl)-3-devinyl chlorin e6 (IV) was the same as step S1 of Embodiment 1.

S2: process for preparing compound $III_2$ was the same as step S2 of Embodiment 2.

S3: according to step S3 of Embodiment 1, compound $III_2$ (150 mg, 0.229 mmol) was reacted with the same equivalent EDCl, 1.2 times of equivalent N-t-butyloxycarboryl-L-lysine tert-butyl ester hydrochloride and 2.4 times of equivalent DIPEA in anhydrous DMF to produce 130 mg of black powder N-[3-(1-n-propoxyl)ethyl-3-devinyl chlorin e6-15$^2$-acyl]-N$^\epsilon$-t-butyloxycarboryl-L-lysine tert-butyl ester ($II_{20}$), with a yield of 60.5%.

Chromatographic data of compound $II_{20}$ was MS (ESI$^+$) m/z: 941.60 [M+H]$^+$ (100%).

S4: according to step S4 of Embodiment 1, compound $II_{20}$ (50 mg, 0.0532 mmol) was reacted with CH$_2$Cl$_2$-TFA (1:1, v/v) to produce 30 mg of black powder N-[3-(1-n-propoxyl) ethyl-3-devinyl chlorin e6-15$^2$-acyl]-L-lysine ($I_{20}$), with a yield of 71.9%.

Chromatographic data of compound $I_{20}$ was MS (ESI*) m/z: 785.62 [M+H]$^+$ (100%).

Embodiment 21: preparation of N-[3-(1-n-hexyloxy)ethyl-3-devinyl chlorin e6-15$^2$-acyl]-L-lysine ($I_{21}$)

S1: process for preparing 3-(1-bromoethyl)-3-devinyl chlorin e6 (IV) was the same as step S1 of Embodiment 1.

S2: process for preparing compound 1113 was the same as step S2 of Embodiment 3.

S3: according to step S3 of Embodiment 1, compound $III_3$ (150 mg, 0.215 mmol) was reacted with the same equivalent EDCl, 1.2 times of equivalent N$^\epsilon$-t-butyloxycarboryl-L-lysine tert-butyl ester hydrochloride and 2.4 times of equivalent DIPEA in anhydrous DMF to produce 116 mg of black powder N-[3-(1-n-hexyloxy)ethyl-3-devinyl chlorin e6-15$^2$-acyl]-N$^\epsilon$-t-butyloxycarboryl-L-lysine tert-butyl ester ($II_{21}$), with a yield of 55.0%.

Chromatographic data of compound $II_{21}$ was: $^1$H NMR (600 MHz, CD$_3$COCD$_3$, δ, ppm): 10.01 (s, 1H), 9.87 (s, 1H), 9.04 (s, 1H), 7.34 (s, 1H), 6.05 (m, 1H), 6.00 (s, 1H), 5.56 (d, J=17.8 Hz, 1H), 5.46 (d, J=17.8 Hz, 1H), 4.69-4.64 (m, 2H), 4.51-4.44 (m, 1H), 3.84 (q, J=7.8 Hz, 2H), 3.76-3.71 (m, 1H), 3.63-3.59 (m, 1H), 3.56 (s, 3H), 3.49 (s, 3H), 3.31 (s, 3H), 2.80 (m, 1H), 2.53-2.31 (m, 3H), 1.75 (d, J=7.2 Hz, 3H), 1.72 (t, J=7.5 Hz, 3H), 1.39 (s, 9H), 1.29 (s, 9H), 1.30-1.17 (m, 12H), 0.74 (t, J=6.5 Hz, 3H), −1.38 (s, 1H), −1.60 (s, 1H). MS (ESI$^+$) 983.58 [M+H]$^+$ (100%).

S4: according to step S4 of Embodiment 1, compound $II_{21}$ (50 mg, 0.0509 mmol) was reacted with CH$_2$Cl$_2$-TFA (1:1, v/v) to produce 28 mg of black powder N-[3-(L-n-hexyloxy) ethyl-3-devinyl chlorin e6-$15^2$-acyl]-L-lysine ($I_{21}$), with a yield of 66.6%, Chromatographic data of compound $I_2$, was: UV-vis $\lambda_{max}$ (CH$_3$OH, nm) ($\epsilon$/M$^{-1}$ cm$^{-1}$): 395 (67600), 497 (6300), 652 (23500). $^1$H NMR (600 MHz, CH$_3$OD, 5, ppm): 10.45 (s, 1H), 10.07 (s, 1H), 9.38 (s, 1H), 6.06 (m, 1H), 5.90 (d, J=17.9 Hz, 1H), 5.43 (d, J=17.9 Hz, 1H), 4.74-4.70 (m, 1H), 4.58-4.52 (m, 2H), 3.90-3.80 (m, 3H), 3.63 (s, 3H), 3.60-3.56 (m, 1H), 3.52 (s, 3H), 3.37 (s, 3H), 3.05 (d, J=6.1 Hz, 2H), 2.81-2.74 (m, 1H), 2.50-2.28 (m, 3H), 2.09 (d, J=6.7 Hz, 3H), 2.00-1.87 (m, 2H), 1.75 (d, J=7.5 Hz, 3H), 1.62 (d, I=7.5 Hz, 3H), 1.51-1.32 (m, 4H), 1.21-1.06 (m, 6H), 0.71 (d, I=7.0 Hz, 3H). MS (ESI$^+$) m/z: 827.64 [M+H]$^+$ (100%),

Embodiment 22: preparation of N-[3-[1-(2-methoxy)ethyoxyl]ethyl-3-devinyl chlorin e6-$15^2$-acyl]-L-lysine ($I_2$)

S1: process for preparing 3-(1-bromoethyl)-3-devinyl chlorin e6 (IV) was the same as step S1 of Embodiment 1.

S2: process for preparing compound III$_4$ was the same as step S2 of Embodiment 4.

S3: according to step S3 of Embodiment 1, compound III$_4$ (150 mg, 0.223 mmol) was reacted with the same equivalent EDCl, 1.2 times of equivalent N$^\epsilon$-t-butyloxycarboryl-L-lysine tert-butyl ester hydrochloride and 2.4 times of equivalent DIPEA in anhydrous DMF to produce 120 mg of black powder N-[3-[1-(2-methoxy)ethyoxyl]ethyl-3-devinyl chlorin e6-$15^2$-acyl]-N$^\epsilon$-t-butyloxycarboryl-L-lysine tert-butyl ester (II$_{22}$), with a yield of 56.2%©.

Chromatographic data of compound II$_{22}$ was MS (ESI$^+$) m/z: 957.52 [M+H]$^+$ (100%).

S4: according to step S4 of Embodiment 1, compound II$_{22}$ (50 mg, 0.0523 mmol) was reacted with CH$_2$Cl$_2$-TFA (1:1, v/v) to produce 26 mg of black powder N-[3-[1-(2-methoxy) ethyoxyl]ethyl-3-devinyl chlorin e6-$15^2$-acyl]-L-lysine (I$_{22}$), with a yield of 62.1%.

Chromatographic data of compound I$_{22}$ was MS (ESI$^+$) m/z: 801.62 [M+H]$^+$ (100%).

Embodiment 23: preparation of N-[3-[1-(2-propoxyl)ethyoxyl]ethyl-3-devinyl chlorin e6-$15^2$-acyl]-L-lysine ($I_{23}$)

S1: process for preparing 3-(1-bromoethyl)-3-devinyl chlorin e6 (IV) was the same as step S1 of Embodiment 1.

S2: process for preparing compound III$_5$ was the same as step S2 of Embodiment 5.

S3: according to step S3 of Embodiment 1, compound III$_5$ (150 mg, 0.214 mmol) was reacted with the same equivalent EDCl, 1.2 times of equivalent N$^\epsilon$-t-butyloxycarboryl-L-lysine tert-butyl ester hydrochloride and 2.4 times of equivalent DIPEA in anhydrous DMF to produce 105 mg of black powder N-[3-[1-(2-propoxyl)ethyoxyl]ethyl-3-devinyl chlorin e6-$15^2$-acyl]-N$^\epsilon$-t-butyloxycarboryl-L-lysine tert-butyl ester (II$_{23}$), with a yield of 49.8%©.

Chromatographic data of compound II$_{23}$ was MS (ESI$^+$) m/z: 985.54 [M+H]$^+$ (100%).

S4: according to step S4 of Embodiment 1, compound II$_{23}$ (50 mg, 0.0508 mmol) was reacted with CH$_2$Cl$_2$-TFA (1:1, v/v) to produce black powder N-[3-[1-(2-propoxyl) ethyoxyl]ethyl-3-devinyl chlorin e6-$15^2$-acyl]-L-lysine (I$_{23}$) 24 mg, with a yield of 57.0%.

Chromatographic data of compound I$_{23}$ was MS (ESI$^+$) m/z: 829.65 [M+H]$^+$ (100%).

Embodiment 24: preparation of N-[3-[1-(3-methoxy)propoxyl]ethyl-3-devinyl chlorin e6-$15^2$-acyl]-L-lysine ($I_{24}$)

S1: process for preparing 3-(1-bromoethyl)-3-devinyl chlorin e6 (IV) was the same as step S1 of Embodiment 1.

S2: process for preparing compound III$_6$, was the same as step S2 of Embodiment 6.

S3: according to step S3 of Embodiment 1, compound III$_6$ (150 mg, 0.219 mmol) was reacted with the same equivalent EDCl, 1.2 times of equivalent N$^\epsilon$-t-butyloxycarboryl-L-lysine tert-butyl ester hydrochloride and 2.4 times of equivalent DIPEA in anhydrous DMF to produce 108 mg of black powder N-[3-[1-(3-methoxy)propoxyl]ethyl-3-devinyl chlorin e6-$15^2$-acyl]-N$^\epsilon$-t-butyloxycarboryl-L-lysine tert-butyl ester (II$_{24}$), with a yield of 50.9%.

Chromatographic data of compound II$_{24}$ was MS (ESI$^+$) m/z: 971.52 [M+H]$^+$ (100%).

S4: according to step S4 of Embodiment 1, compound II$_{24}$ (50 mg, 0.0515 mmol) was reacted with CH$_2$Cl$_2$-TFA (1:1, v/v) to produce 25 mg of black powder N-[3-[1-(3-methoxy) propoxyl]ethyl-3-devinyl chlorin e6-$15^2$-acyl]-L-lysine (I$_{24}$), with a yield of 59.6%.

Chromatographic data of compound I$_{24}$ was MS (ESI$^+$) m/z: 815.66 [M+H]$^+$ (100%).

Embodiment 25: preparation of N-[3-[1-(4-methoxy)butoxy]ethyl-3-devinyl chlorin e6-$15^2$-acyl]-1-lysine ($I_{25}$)

S1: process for preparing 3-(1-bromoethyl)-3-devinyl chlorin e6 (IV) was the same as step S1 of Embodiment 1.

S2: process for preparing compound III$_7$ was the same as step S2 of Embodiment 7.

S3: according to step S3 of Embodiment 1, compound III$_7$ (150 mg, 0.214 mmol) was reacted with the same equivalent EDCl, 1.2 times of equivalent N$^\epsilon$-t-butyloxycarboryl-L-lysine tert-butyl ester hydrochloride and 2.4 times of equivalent DIPEA in anhydrous DMF to produce 105 mg of black powder N-[3-[1-(4-methoxy)butoxy]ethyl-3-devinyl chlorin e6-$15^2$-acyl]-N$^\epsilon$-t-butyloxycarboryl-L-lysine tert-butyl ester (II$_{25}$), with a yield of 49.8%.

Chromatographic data of compound II$_{25}$ was MS (ESI$^+$) m/z: 985.58 [M+H]$^+$ (100%).

S4: according to step S4 of Embodiment 1, compound II$_{25}$ (50 mg, 0.0508 mmol) was reacted with CH$_2$Cl$_2$-TFA (1:1, v/v) to produce 23 mg of black powder N-[3-[1-(4-methoxy) butoxy]ethyl-3-devinyl chlorin e6-$15^2$-acyl]-L-lysine (I$_{25}$), with a yield of 54.7%.

Chromatographic data of compound I$_{25}$ was MS (ESI$^+$) m/z: 829.68 [M+H]$^+$ (100%).

Embodiment 26: preparation of N-[3-[1-(2-(2-methoxy)ethyoxyl)ethyoxyl]ethyl-3-devinyl chlorin e6-$15^2$-acyl]-lysine ($I_{26}$)

S1: process for preparing 3-(1-bromoethyl)-3-devinyl chlorin e6 (IV) was the same as step S1 of Embodiment 1.

S2: process for preparing compound III$_4$ was the same as step S2 of Embodiment 8.

S3: according to step S3 of Embodiment 1, compound III (150 mg, 0.209 mmol) was reacted with the same equivalent EDCl, 1.2 times of equivalent N$^\epsilon$-t-butyloxycarboryl-L-lysine tert-butyl ester hydrochloride and 2.4 times of equivalent DIPEA in anhydrous DMF to produce 95 mg of black powder N-[3-[1-(2-(2-methoxy)ethyoxyl)ethyoxyl]ethyl-3- devinyl chlorin e6-15$^2$-acyl]-N$^\epsilon$-t-butyloxycarboryl-L-lysine tert-butyl ester (II$_{26}$), with a yield of 45.3%.

Chromatographic data of compound II$_{26}$ was MS (ESI$^+$) m/z: 1001.54 [M+H]$^+$ (100%).

S4: according to step S4 of Embodiment 1, compound II$_{26}$ (50 mg, 0.05 mmol) was reacted with CH$_2$Cl$_2$-TFA (1:1, v/v) to produce 22 mg of black powder N-[3-[1-(2-(2-methoxy)ethyoxyl)ethyoxyl]ethyl-3-devinyl chlorin e6-15$^2$-acyl]-L-lysine (I$_{26}$), with a yield of 52.1%.

Chromatographic data of compound I$_{26}$ was MS (ESI$^+$) m/z: 845.64 [M+H]$^+$ (100%).

Embodiment 27: preparation of N-[3-[1-(2-(2-(2-methoxy)ethyoxyl)ethyoxyl)ethyoxyl]ethyl-3-devinyl chlorin e6-15$^2$-acyl]-L-lysine (I$_{27}$)

S1: process for preparing 3-(1-bromoethyl)-3-devinyl chlorin e6 (IV) was the same as step S1 of Embodiment 1.

S2: process for preparing compound III$_9$ was the same as step S2 of Embodiment 9.

S3: according to step S3 of Embodiment 1, compound III$_9$ (150 mg, 0.197 mmol) was reacted with the same equivalent EDCl, 1.2 times of equivalent N$^\epsilon$-t-butyloxycarboryl-L-lysine tert-butyl ester hydrochloride and 2.4 times of equivalent DIPEA in anhydrous DMF to produce 86 mg of black powder N-[3-[1-(2-(2-(2-methoxy)ethyoxyl) ethyoxyl)ethyoxyl]ethyl-3-devinyl chlorin e6-15$^2$-acyl]-N$^\epsilon$-t-butyloxycarboryl-L-lysine tert-butyl ester (II$_{27}$), with a yield of 41.7%.

Chromatographic data of compound II$_{27}$ was MS (ESI$^+$) m/z: 1045.56 [M+H]$^+$ (100%).

S4: according to step S4 of Embodiment 1, compound II$_{27}$ (50 mg, 0.0479 mmol) was reacted with CH$_2$Cl$_2$-TFA (1:1, v/v) to produce 20 mg of black powder N-[3-[1-(2-(2-(2-methoxy)ethyoxyl)ethyoxyl)ethyoxyl]ethyl-3-devinyl chlorin e6-15$^2$-acyl]-'L-lysine (I$_{27}$), with a yield of 47.0%.

Chromatographic data of compound I$_{27}$ was MS (ESI$^+$) m/z: 889.58 [M+H]$^+$ (100%).

Embodiment 28: In Vitro PDT Anti-Tumor Activity of Chlorin e6 Ether Amino Acid Derivatives 1. Materials Human non-small cell lung cancer cellA549 and mice melanoma cell B16-F10 provided by Cell bank of Shanghai in Chinese Academy of Sciences were selected as cell strains.

660 nm semiconductor laser therapeutic equipments manufactured by Baifei biomedical company of Shanghai was selected as a laser light source, with the largest output power of 2 W.

2. Methods

1) Cell strains of tumors: culture of human non-small cell lung cancer cell (A549) and mice melanoma cell (B16-F10): frozen cells were taken out of liquid nitrogen, placed in a water bath at 42° C. The cells were thawed quickly, transferred into medium containing fresh fetal cow serum [RPMI 1640 or DMEM+10% (v/v) FBS+10% (v/v)+1% (v/v) double resistant (penicillin+streptomycin), and placed in an incubator containing CO$_2$ at 37° C. for incubating. The medium was renewed once every two days.

2) Preparation of reagents: compounds of the present application to be tested and positive control drug Talaporfin were dissolved in a suitable amount of 0.1 M NaOH, adjusted pH to 7.4 by 0.1 M HCl. Normal saline was added to prepare drug stock solution in a suitable concentration.

3) Detecting darktoxicity and PDT killing effects to the two tumor cells of compounds to be tested and positive control drug: 100 μL of 5×10$^3$/mL cell suspension was added into each well of 96-well plate, placed in a incubator at 37° C., 5% CO$_2$ for 24 h. after removing cell medium, fresh mediums containing different concentration of samples were added, opened with three complex holes, and incubated for 24 h at 37° C. and 5% CO$_2$ (volume concentration). After adding fresh medium, no light irradiated (darktoxicity) or 660 nm wavelength laser was used to irradiate (light dose was 8 J/cm$^2$) (phototoxicity). Cells were incubated for another 24 h. Cell medium containing drugs were removed and fresh medium was added. 200 μL medium containing 10% (v/v) CCK-8 (Dojindo Laboratories, Japan) was added into each well, and incubated for 1.5 h. Microplate reader (Tecan, Switzerland) was used to measure absorbance of each well at a wavelength of 450 nm.

3. Results

Darktoxicity and PDT killing effects on tumor cells in vitro of parts of preferable target compounds of the present application were shown in Table 2.

TABLE 2 median inhibitory concentration IC$_{50}$ (μM) to tumor cells of parts of target compounds

| | A549 | | | B16-F10 | | |
|---|---|---|---|---|---|---|
| Compounds | Darktoxicity (IC$_{50}$, μM) | Phototoxicity (IC$_{50}$, μM) | Ratio of Darktoxicity and Phototoxicity | Darktoxicity (IC$_{50}$, μM) | Phototoxicity (IC$_{50}$, μM) | Ratio of Darktoxicity and Phototoxicity |
| I$_1$ | >300 | 1.32 | >227.27 | 210.82 | 2.06 | 102.34 |
| I$_2$ | >300 | 1.04 | >288.46 | 186.08 | 1.48 | 125.73 |
| I$_3$ | 284.92 | 0.65 | 438.34 | 191.93 | 0.89 | 215.65 |
| I$_4$ | 298.56 | 1.17 | 255.18 | 183.40 | 1.61 | 113.91 |
| I$_7$ | 273.38 | 0.86 | 317.88 | 165.75 | 1.04 | 159.38 |
| I$_8$ | 286.82 | 1.01 | 283.98 | 174.56 | 1.43 | 122.07 |
| I$_{10}$ | >300 | 1.63 | >184.05 | 189.31 | 2.15 | 88.05 |
| I$_{11}$ | 278.22 | 1.12 | 248.41 | 172.67 | 1.63 | 105.93 |
| I$_{12}$ | 256.40 | 0.72 | 356.11 | 180.72 | 0.93 | 194.32 |
| I$_{13}$ | 267.37 | 1.25 | 213.90 | 159.84 | 1.72 | 92.93 |
| I$_{16}$ | 249.78 | 0.97 | 257.51 | 153.29 | 1.09 | 140.63 |
| I$_{17}$ | 264.69 | 1.10 | 240.63 | 168.78 | 1.52 | 111.04 |
| I$_{19}$ | >300 | 1.92 | >156.25 | 192.46 | 2.28 | 84.41 |
| I$_{20}$ | >300 | 1.33 | >225.56 | 162.53 | 1.75 | 92.87 |
| I$_{21}$ | 292.54 | 0.79 | 370.30 | 179.88 | 1.05 | 171.31 |
| I$_{22}$ | 258.36 | 1.47 | 175.76 | 170.44 | 1.91 | 89.24 |
| I$_{25}$ | 239.83 | 1.08 | 222.06 | 162.57 | 1.16 | 140.15 |
| I$_{26}$ | 247.98 | 1.23 | 201.61 | 175.69 | 1.67 | 105.20 |
| Talaporfin | 276.54 | 8.86 | 31.21 | 169.80 | 10.74 | 15.81 |

Results in Table 2 showed that under the light dose of 8 J/cm$^2$, all tested compounds showed good PDT anti-cancer activity to two tumor cell strains. Further, both activity (phototoxicity) and the ratio of darktoxicity-phototoxicity (treatment index) were better than that of similar photosensitizer Talaporfin. It was demonstrated that compared with Talaporfin the toxicity and activity of these new compounds were insulated, and possessed better treatment index.

Initial structure-function relationship showed that the PDT anti-cancer activity of tested target compounds increased over the length of carbon chains of ether, with the length of 6 carbon atoms was best. That was, the activity of amino acid derivatives of chlorin e6 n-hexyl ether (I$_3$, I$_{12}$ and I$_{21}$) are best. Further, when methylene in carbon chain of ether was substituted by oxygen atom, the activity decreased. Regarding phototoxicity to two tumor cell strains: $I_7<I_3$, $I_{16}<I_{12}$, $I_{25}<I_{21}$. In addition, the type of amino acids might have some influence on the activity and darktoxicity, wherein aspartic acid was the most preferably. That was, aspartic acid derivatives of chlorin e6 n-hexyl ether $I_3$ had the highest PDT anti-tumor activity and the ratio of darktoxicity-phototoxicity. The PDT anti-tumor activity to human non-small cell lung cancer cellA549 and mice melanoma cell B16-F10 was 13.63 and 12.07 times that of Talaporfin, respectively. Further, the ratio of darktoxicity-phototoxicity to the above two tumor cells was 14.04 and 13.64 times that of Talaporfin, respectively.

Therefore, it was possible that chlorin e6 ether amino acid derivatives of the present application may be an anti-tumor drug with better treatment effect and lower toxicity than Talaporfin.

It to be noted that the above Embodiments are provided just for explaining the technical solutions of the present application, rather than limiting it. Although the present application has been set forth in detail referring to the above Embodiments, it can be understood by those skilled in the art that technical solutions disclosed in the above Embodiments can be modified or replaced. However, these modification and replacement should fall into the protection scope of the present application without departing from the substantial spirit of technical solutions of the above Embodiments.

The invention claimed is:

1. A new chlorin e6 derivative and pharmaceutically acceptable salt thereof, wherein the chlorin e6 derivative comprises general structural formula I and optical isomers of the general structural formula I,

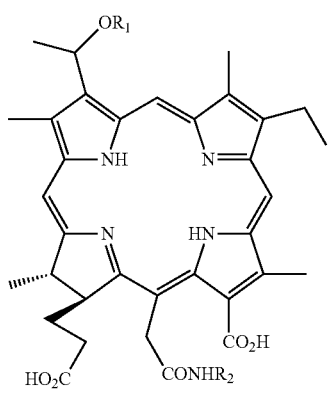

I in the above general structural formula I, $R_1$ represents H, a lower alkyl, a higher alkyl, $(CH_2)_mOR_3$ or $(CH_2CH_2O)_kR_4$, wherein the higher alkyl is a linear or branched alkyl containing 7-18 carbon atoms, $R_3$ and $R_4$ independently represent H, a lower alkyl, m and k independently represent any integers between 2 and 6, in $R_1$, $R_3$ and $R_4$, the lower alkyl is a linear or branched alkyl containing 1-6 carbon atoms, $R_2$ represents an amino acid residue.

2. The chlorin e6 derivative and pharmaceutically acceptable salt thereof according to claim 1, wherein in the general structural formula I, $R_1$ represents $CH_3$, $C_3H_7$, $C_6H_{13}$, $(CH_2)_2OCH_3$, $(CH_2)_2OC_3H_7$, $(CH_2)_3OCH_3$, $(CH_2)_4OCH_3$, $(CH_2CH_2O)_2CH_3$ or $(CH_2CH_2O)_3CH_3$, in the general structural formula I, $R_2$ represents aspartic acid, glutamic acid or lysine residue.

3. The chlorin e6 derivative and pharmaceutically acceptable salt thereof according to claim 2, wherein the general structural formula I is selected from any one of $I_1$-$I_{27}$, in $I_1$-$I_{27}$, the structure of $R_1$ and $R_2$ is shown as follows, respectively: compounds $R_1$ $R_2$ $I_1$ $CH_3$ $CH(CO_2H)CH_2CO_2H$
$I_2$ n-$C_3H_7$ $CH(CO_2H)CH_2CO_2H$
$I_3$ n-$C_6H_{13}$ $CH(CO_2H)CH_2CO_2H$
$I_4$ $(CH_2)_2OCH_3$ $CH(CO_2H)CH_2CO_2H$
$I_5$ $(CH_2)_2O$-n-$C_3H_7$ $CH(CO_2H)CH_2CO_2H$
$I_6$ $(CH_2)_3OCH_3$ $CH(CO_2H)CH_2CO_2H$
$I_7$ $(CH_2)_4OCH_3$ $CH(CO_2H)CH_2CO_2H$
$I_8$ $(CH_2CH_2O)_2CH_3$ $CH(CO_2H)CH_2CO_2H$
$I_9$ $(CH_2CH_2O)_3CH_3$ $CH(CO_2H)CH_2CO_2H$
$I_{10}$ $CH_3$ $CH(CO_2H)CH_2CH_2CO_2H$
$I_{11}$ n-$C_3H_7$ $CH(CO_2H)CH_2CH_2CO_2H$
$I_{12}$ n-$C_6H_{13}$ $CH(CO_2H)CH_2CH_2CO_2H$
$I_{13}$ $(CH_2)_2OCH_3$ $CH(CO_2H)CH_2CH_2CO_2H$
$I_{14}$ $(CH_2)_2O$-n-$C_3H_7$ $CH(CO_2H)CH_2CH_2CO_2H$
$I_{15}$ $(CH_2)_3OCH_3$ $CH(CO_2H)CH_2CH_2CO_2H$
$I_{16}$ $(CH_2)_4OCH_3$ $CH(CO_2H)CH_2CH_2CO_2H$
$I_{17}$ $(CH_2CH_2O)_2CH_3$ $CH(CO_2H)CH_2CH_2CO_2H$
$I_{18}$ $(CH_2CH_2O)_3CH_3$ $CH(CO_2H)CH_2CH_2CO_2H$
$I_{19}$ $CH_3$ $CH(CO_2H)CH_2CH_2CH_2CH_2NH_2$
$I_{20}$ n-$C_3H_7$ $CH(CO_2H)CH_2CH_2CH_2CH_2NH_2$
$I_{21}$ n-$C_6H_{13}$ $CH(CO_2H)CH_2CH_2CH_2CH_2NH_2$
$I_{22}$ $(CH_2)_2OCH_3$ $CH(CO_2H)CH_2CH_2CH_2CH_2NH_2$
$I_{23}$ $(CH_2)_2O$-n-$C_3H_7$ $CH(CO_2H)CH_2CH_2CH_2CH_2NH_2$
$I_{24}$ $(CH_2)_3OCH_3$ $CH(CO_2H)CH_2CH_2CH_2CH_2NH_2$
$I_{25}$ $(CH_2)_4OCH_3$ $CH(CO_2H)CH_2CH_2CH_2CH_2NH_2$
$I_{26}$ $(CH_2CH_2O)_2CH_3$ $CH(CO_2H)CH_2CH_2CH_2CH_2NH_2$
$I_{27}$ $(CH_2CH_2O)_3CH_3$ $CH(CO_2H)CH_2CH_2CH_2CH_2NH_2$ wherein, n represents "normal-".

4. The chlorin e6 derivative and pharmaceutically acceptable salt thereof according to claim 3, wherein the pharmaceutically acceptable salt is an inorganic alkali salt.

5. A process for preparing the chlorin e6 ether amino acid derivative according to claim 1, comprising:
S11: using chlorin e6 as a raw material,
S12: conducting an addition reaction between 3-vinyl of chlorin e6 and halogen hydride, then alcoholizing the addition product by $R_1OH$,
S13: conducting a peptide condensation reaction between 15-carboxylethyl in chlorin e6 and amino acid to prepare the chlorin e6 ether amino acid derivative.

6. The process for preparing the chlorin e6 ether amino acid derivative according to claim 5, wherein in the step S13, 15-carboxylethyl in chlorin e6 is reacted with 1-(3-dimethylamino propyl)-3-ethyl carbodiimide hydrochloride and carboxyl tert-butyl protected or non-α-amino t-butyloxycarbonyl protected L-amino acid hydrochloride $R_2'NH_2$.HCl to produce carboxyl and amino protected chlorin e6 ether amino acid derivatives, then the carboxyl and amino protected chlorin e6 ether amino acid derivatives are deprotected of tert-butyl or t-butyloxycarbonyl to prepare the chlorin e6 ether amino acid derivative,
wherein $R_2'$ represents a protected amino acid residue $R_2$.

7. The process for preparing the chlorin e6 ether amino acid derivative according to claim 1, comprising:
S1: reacting chlorin e6 (V) with HBr in glacial acetic acid at room temperature for 10-30 h to produce compound IV,
S2: reacting compound IV with $R_1OH$ in the presence of $K_2CO_3$ to produce compound III,
S3: in N,N-dimethylformamide, reacting compound III with 1-(3-dimethylamino propyl)-3-ethyl carbodiimide hydrochloride at room temperature for 2-6 h, then in the presence of N,N-dimethyl isopropyl amine, reacting with carboxyl tert-butyl protected or non-α-amino t-butyloxycarbonyl protected L-amino acid hydrochloride $R_2'NH_2$.HCl to produce carboxyl and amino protected chlorin e6 ether amino acid derivatives II, where R₂' represents a protected amino acid residue R₂, and
S4: deprotecting compound II of tert-butyl or t-butyloxy-carbonyl by trifluoroacetic acid to produce the chlorin e6 ether amino acid derivative of formula (I)

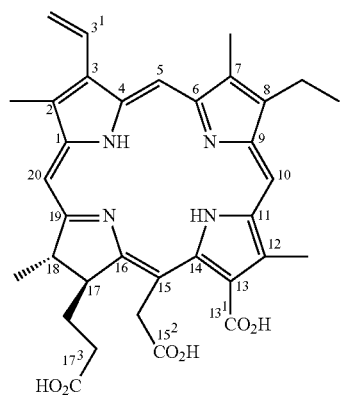

chlorin e6 (V)

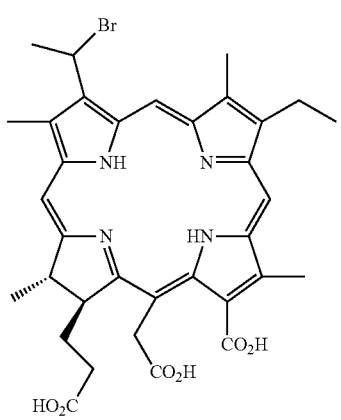

(IV)

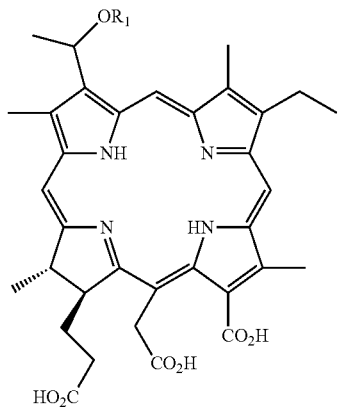

(III)

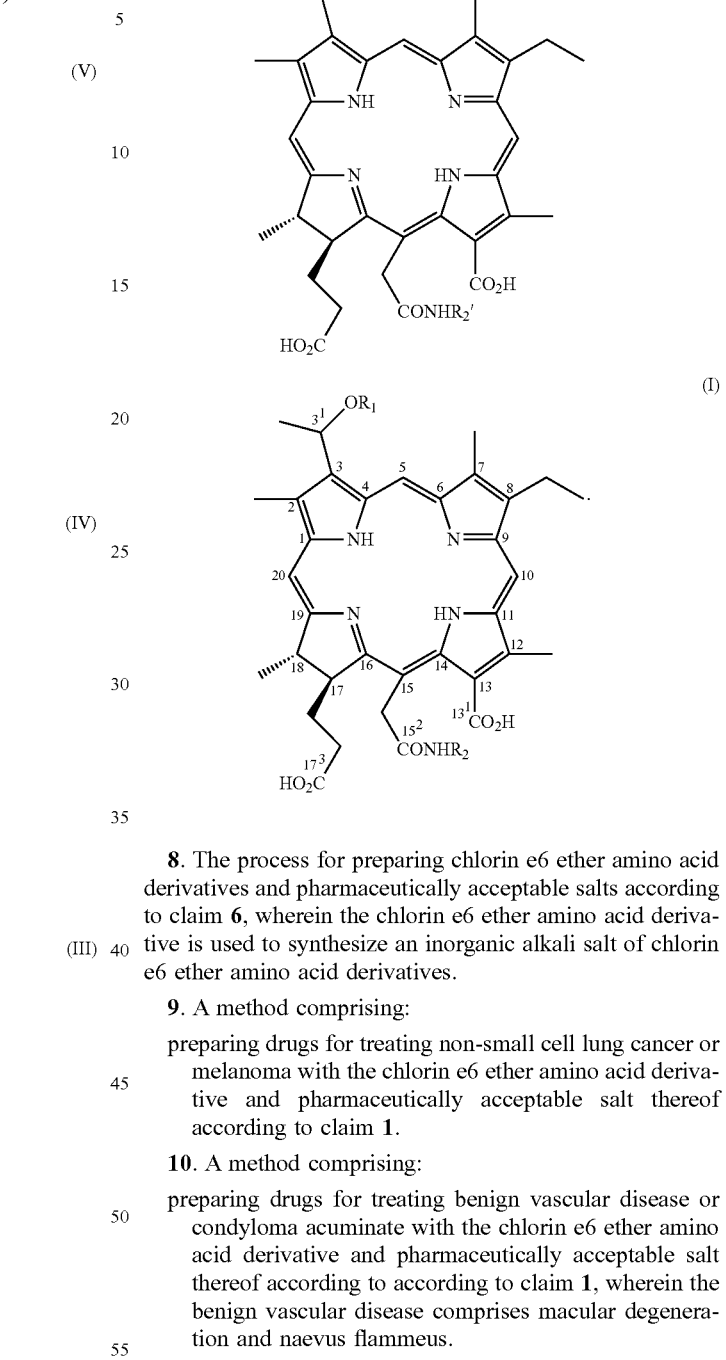

(II)

(I)

8. The process for preparing chlorin e6 ether amino acid derivatives and pharmaceutically acceptable salts according to claim 6, wherein the chlorin e6 ether amino acid derivative is used to synthesize an inorganic alkali salt of chlorin e6 ether amino acid derivatives.

9. A method comprising:
preparing drugs for treating non-small cell lung cancer or melanoma with the chlorin e6 ether amino acid derivative and pharmaceutically acceptable salt thereof according to claim 1.

10. A method comprising:
preparing drugs for treating benign vascular disease or condyloma acuminate with the chlorin e6 ether amino acid derivative and pharmaceutically acceptable salt thereof according to according to claim 1, wherein the benign vascular disease comprises macular degeneration and naevus flammeus.

* * * * *